United States Patent
Page et al.

(10) Patent No.: US 12,018,265 B2
(45) Date of Patent: *Jun. 25, 2024

(54) NUCLEIC ACID ENCODING N-METHYLPUTRESCINE OXIDASE AND USES THEREOF

(71) Applicant: 22nd Century Limited, LLC, Williamsville, NY (US)

(72) Inventors: Jonathan E Page, Saskatoon (CA); Enwu Liu, Saskatoon (CA)

(73) Assignee: 22nd Century Limited, LLC, Buffalo, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/847,138

(22) Filed: Jun. 22, 2022

(65) Prior Publication Data

US 2023/0029030 A1  Jan. 26, 2023

Related U.S. Application Data

(60) Continuation of application No. 16/877,401, filed on May 18, 2020, now Pat. No. 11,396,656, which is a continuation of application No. 16/054,711, filed on Aug. 3, 2018, now Pat. No. 10,689,658, which is a continuation of application No. 15/242,129, filed on Aug. 19, 2016, now Pat. No. 10,041,084, which is a division of application No. 13/774,902, filed on Feb. 22, 2013, now Pat. No. 9,422,532, which is a division of application No. 12/305,483, filed as application No. PCT/IB2007/003550 on Jun. 19, 2007, now Pat. No. 8,410,341.

(60) Provisional application No. 60/901,654, filed on Feb. 16, 2007, provisional application No. 60/814,542, filed on Jun. 19, 2006.

(51) Int. Cl.
*C12N 15/82* (2006.01)
*A24B 13/00* (2006.01)
*A24B 15/12* (2006.01)
*C12N 9/06* (2006.01)

(52) U.S. Cl.
CPC .......... *C12N 15/8243* (2013.01); *A24B 13/00* (2013.01); *A24B 15/12* (2013.01); *C12N 9/0022* (2013.01); *C12Y 104/03006* (2013.01)

(58) Field of Classification Search
CPC ................................................. C12N 15/8243
See application file for complete search history.

(56) References Cited

U.S. PATENT DOCUMENTS

| | | | |
|---|---|---|---|
| 4,407,956 A | 10/1983 | Howell | |
| 5,260,205 A | 11/1993 | Nakatani et al. | |
| 5,369,023 A | 11/1994 | Nakatani et al. | |
| 5,459,252 A | 10/1995 | Conkling et al. | |
| 5,466,785 A | 11/1995 | De Framond | |
| 5,633,363 A | 5/1997 | Colbert et al. | |
| 5,837,848 A | 11/1998 | Ely et al. | |
| 5,837,876 A | 11/1998 | Conkling et al. | |
| 6,018,099 A | 1/2000 | De Framond | |
| 6,423,520 B1 | 7/2002 | Conkling et al. | |
| 6,586,661 B1 | 7/2003 | Conkling et al. | |
| 6,602,986 B1 | 8/2003 | Stemmer et al. | |
| 7,229,829 B2 | 6/2007 | Dinesh Kumar et al. | |
| 8,410,341 B2 * | 4/2013 | Page ................ | C12N 15/8243 536/23.6 |
| 9,102,948 B2 | 8/2015 | Hashimoto et al. | |
| 9,422,533 B2 * | 8/2016 | Page ............... | A24B 15/12 |
| 10,041,084 B2 | 8/2018 | Page et al. | |
| 2003/0106105 A1 | 6/2003 | Hoffmann et al. | |
| 2004/0031072 A1 | 2/2004 | La Rosa et al. | |
| 2004/0107455 A1 | 6/2004 | Rommens et al. | |
| 2005/0010974 A1 | 1/2005 | Milligan et al. | |
| 2005/0097633 A1 | 5/2005 | Diehn et al. | |
| 2009/0055964 A1 | 2/2009 | Gelesko | |

FOREIGN PATENT DOCUMENTS

| | | |
|---|---|---|
| WO | WO 00/52168 | 9/2000 |
| WO | WO 01/59086 A2 | 8/2001 |
| WO | WO-02/10210 A2 | 2/2002 |
| WO | WO 02/38588 A2 | 5/2002 |
| WO | WO 03/013226 A2 | 2/2003 |
| WO | WO 2004/076625 A2 | 9/2004 |
| WO | WO 2005/018307 A1 | 3/2005 |
| WO | WO 2006/109197 | 10/2006 |

OTHER PUBLICATIONS

Non-Final Office Action issued in related U.S. Appl. No. 12/305,483, dated Apr. 18, 2012.
Notice of Allowance issued in related U.S. Appl. No. 12/305,483, dated Dec. 24, 2012.
Non-Final Office Action issued in related U.S. Appl. No. 13/774,933, dated Oct. 1, 2015.
GenBank Accession BT000029 (At2g42490) created Sep. 19, 2002.
Naconsie, et al., "Molecular Evolution of N-Methylputrescine Oxidase in Tobacco," Plant Cell and Physiology, vol. 55, No. 2, pp. 436-444 (2014).
Liu Huashan et al., "Physiological Effects of Exogenous Plant Growth Regulators on Changes in Nicotine Content and Some Enzyme Activities in Tobacco Roots," vol. 41, No. 3, p. 319-321, (2005), [Abstract].
Chinese Office Action issued in related Chinese Patent Application No. 200780030894.7, dated Sep. 29, 2012.

(Continued)

*Primary Examiner* — Russell Kallis
(74) *Attorney, Agent, or Firm* — Foley & Lardner LLP

(57) ABSTRACT

The gene encoding N-methylputrescine oxidase (MPO) and constructs comprising such DNA are provided, including methods of regulating MPO expression independently or with other alkaloid biosynthesis genes to modulate alkaloid production in plants and host cells. MPO genes or fragments thereof are useful for reducing pyrrolidine or tropane alkaloid production in plants, for increasing pyrrolidine or tropane alkaloid production in plants, and for producing an MPO enzyme in host cells.

18 Claims, 13 Drawing Sheets

Specification includes a Sequence Listing.

(56) References Cited

OTHER PUBLICATIONS

Notice of Allowance issued in related U.S. Appl. No. 13/774,933, dated Apr. 15, 2016.
Akira Katoh et al., "Molecular Cloning of N-methylputrescine Oxidase from Tobacco", Plant Cell Physiol. 48(3): 550-554, 2007.
David O'Hagan, "Pyrrole, pyrrolidine, pyridine, piperidine and tropane alkaloids", Nat. Prod. Rep. 2000, 17, 435-446.
English Translation of First Office Action Chinese Patent Application No. 200780030894.7 dated Dec. 13, 2011.
GenBank Accession gi: 52307027 published Jun. 28, 1999.
International Search Report PCT/IB2007/003550 dated May 6, 2008.
J. Saunders et al., Plant Physiology, 1979, vol. 64, pp. 236-240.
Non-Final Office Action U.S. Appl. No. 12/305,483 dated Aug. 2, 2011.
Non-Final Office Action U.S. Appl. No. 12/305,483 dated Mar. 17, 2011.
T. Wu et al., GenBank Accession gi: 5230727; Jun. 28, 1999.
W. Russell Mclauchlan et al., "The purification and immunocharacterisation of N-methylputrescine oxidase from transformed root cultures of *Nicotiana tabacum* L. cv SC58", Planta (1993) 191:440-445.
William G. Heim et al., "Cloning and characterization of a Nicotiana tabacum methylputrescine oxidase transcript", Phytochemistry 68 (2007) 454-463.
Songstad, et al., "Advances in Alternative DNA delivery techniques," *Plant Cell, tissue and Organ Culture*, vol. 40, pp. 1-15 (1995).
Steppuhn et al., "Nicotine's Defensive Function in Nature", PLoS Biology, Aug. 2004, vol. 2, Issue 8, 1074-1080 (Aug. 2004).
Thompson et al., "Characterization of the herbicide-resistance gene bar from Streptomyces hygroscopicus", The EMBO Journal, vol. 6, No. 9, pp. 2519-2523, 1987.
Zhu et al., "Targeted manipulation of maize genes in vivo using chimeric RNA/DNA oligonucleotides", Proc. Natl. Acad. Sci. USA, vol. 96, pp. 8768-8773, (Jul. 1999).
Zoller et al., "Oligonucleotide-directed mutagenesis using M13-derived vectors: an efficient and general procedure for the production of point mutations in any fragment of DNA", Nucleic Acids Research, vol. 10, No. 20, pp. 6487-6500 (1982).
Winz, et al., "Molecular Interactions between the Specialist Herbivore *Manduca sexta* (Lepidoptera, Sphingidae) and Its Natural Host *Nicotiana attenuata*. IV. Insect-Induced Ethylene Reduces Jasmonate-Induced Nicotine Accumulation by Regulating Putrescine N-Methyltransferase Transcripts1,2," *Plant Physiology*, vol. 125, pp. 2189-2202 (Apr. 2001).
Watson, et al., "Biosynthesis of anabasine in transformed root cultures of *Nicotiana* species," *J. Chem. Soc. Perkin Trans.*, vol. 1, pp. 2607-2610 (1990). [Abstract].
Walton, et al., "Diamine oxidation and alkaloid production in transformed root cultures of Nicotiana tabacum," *Phytochemistry*, vol. 29, pp. 1455-1457 (1990).
Stam et al., "Distinct features of post-transcriptional gene silencing by antisense transgenes in single copy and inverted T-DNA repeat loci," *Plant J.*, vol. 21, pp. 27-42 (2000).
Ramakers, et al., "Assumption-free analysis of quantitative real-time polymerase chain reaction(PCR) data," *Neuroscience Letters*, vol. 339, pp. 62-66 92003).
Katavic et al., "In planta transformation of *Arabidopsis thaliana*," Mol. Gen. Genet. 245:363-370 (1994).
Rhodes et al., "Genetically Transformed Maize Plants from Protoplasts", Science, vol. 240, pp. 204-207 (Apr. 1988).
Sato et al., "Metabolic engineering of plant alkaloids biosynthesis," *PNAS*, vol. 98, No. 1, pp. 367-372 (Jan. 2001).
Shimamoto et al., "Fertile transgenic rice plants regenerated from transformed protoplasts", Nature, vol. 338, Mar. 16, pp. 274-276 (1989).
Shoji et al., "Expression patterns of two tobacco isoflavone reductase-like genes and their possible roles in secondary metabolism in tobacco", Plant Molecular Biology 50: 427-440, 2002.

Shoji et al., "Jasmonate Induction of Putrescine N-Methyltransferase Genes in the Root of Nicotiana sylvestris", Plant Cell Physiol. 41(7): 831-839 (2000).
Siminszky, et al., "Conversion of nicotine to nornicotine in Nicotiana tabacum is mediated by CYP82E4, a cytochrome P450 monooxygenase," *PNAS*, vol. 102, No. 41, pp. 14919-14924 (Oct. 2005).
Sinclair et al., "Analysis of wound-induced gene expression in *Nicotiana* species with contrasting alkaloid profiles", Functional Plant Biology, 31, 721-729 (2004).
Sinclair et al., "Molecular characterization of puinolinate phosphoribosyltransferase (QPRTase) in Nicotiana", Plant Molecular Biology, 44: 603-617, (2000).
Henikoff et al., "Tilling: Traditional Mutagenesis Meets Functional Genomics," *Plant Physiology*, vol. 135, pp. 630-636 (Jun. 2004).
Hibi et al., "Gene Expression in Tobacco Low-Nicotine Mutants", The Plant Cell, vol. 6, pp. 723-735 (May 1994).
Hsu et al., "Phloem Mobility of Xenobiotics VI. A Phloem-Mobile Pro-nematicide Based on Oxamyl Exhibiting Root-Specific Activation in Transgenic Tobacco", Pestic. Sci., 44, pp. 9-19 (1995).
Hwang et al., "An *Arabidopsis thaliana* root-specific kinase homolog is induced by dehydration, ABA, and NaCl", The Plant Journal (1995), 8(1), 37-43.
Liu et al., "Tobacco Rar1, EDS1 and NPR1/NIM1 like genes are required for N-mediated resistance to tobacco mosaic virus," *The Plant Journal*, vol. 30, No. 4, pp. 415-429 (2002).
Mayfield et al., "Expression of human antibodies in eukaryotic micro-algae", Vaccine, 23, (2005), 1828-1832.
Potrykus, "Gene Transfer to Plants: Assessment of Published Approaches and Results," *Annual Review, Plant Physiol., Plant Mol. Biol.*, vol. 42, pp. 205-225 (1991).
Ratcliff, et al., "Tobacco rattle virus as a vector for analysis of gene function by silencing," *The Plant Journal*, vol. 25, No. 2, pp. 237-245 (2001).
Gavilano et al., "Genetic Engineering of *Nicotiana tabacum* for Reduced Nornicotine Content," *J. Agric. Food Chem.* 54, 9071-9078 (2006). {Abstract}.
Gossen et al., "Tight control of gene expression in mammalian cells by tetracycline-responsive promoters", Proc. Natl. Acad. Sci. USA, vol. 89, pp. 5547-5551, 1992.
Guillon et al., Hairy root research: recent scenario and exciting prospects, *Curr. Opin. Plant Biol.* 9, pp. 341-346 (2006).
Hamilton, et al., "Species of small antisense RNA in post-transcriptional gene silencing in plants," *DC Science*, vol. 286, pp. 950-952 (1999). [Abstract].
Hashimoto et al., "Diamine Oxidase from Cultured Roots of Hyoscyamus niger," *Plant Physiol.*, vol. 93, pp. 216-221 (1990).
Hashimoto et al., "Alkaloid Biogenesis: Molecular Aspects," *Annu. Rev. Plant Physiol., Plant Mol. Biol.*, vol. 45, pp. 257-285 (1994).
Haslam et al., Purification of N-methylputrescine oxidase from Nicotiana, *Phytochemistry*, pp. 4075-4079 (1992).
Hecht et al., "Tobacco-Specific Nitrosamines: Occurrence, Formation, Carcinogenicity, and Metabolism", Accounts of Chemical Research, 1979 American Chemical Society, vol. 12, pp. 92-98 (1979).
Broothaerts et al., "Gene transfer to plants by diverse species of bacteria", Nature, vol. 433, pp. 629-633 (Feb. 2005).
Chintapakorn et al., "Antisense-mediated down-regulation of putrescine N-methyltransferase activity in transgenic *Nicotiana tabacum* L. can lead to elevated levels of anatabine at the expense of nicotine", Plant Molecular Biology 53: 87-105 (2003).
Davies, et al., "Quinoprotein characteristics of N-methylputrescine oxidase from tobacco roots," Phytochemistry, vol. 28, pp. 1573-1578 (1989). [Abstract].
Dawson RF, The Localization of the Nicotine Synthetic Mechanism in the Tobacco Plant, *Science* 94: pp. 396-397 (Oct. 1941). [Abstract].
DeBlock et al., Transformation of *Brassica napus* and *Brassica oleracea* Using *Agrobacterium tumefaciens* and the Expression of the bar and neo Genes in the Transgenic Plants, *Plant Physiol.* 91:694-701 (Jun. 1989).
Depicker and van Montagu, "Post-transcriptional gene silencing in plants," *Curr Opin Cell Biol* 9, pp. 373-382 (1997).

(56) References Cited

OTHER PUBLICATIONS

Feth et al., "Determination of methylputrescine oxidase by high performance liquid chromatography," *Phytochemistry*, vol. 24, pp. 1653-1655 (1985). {Abstract}.

Archer et al., "Strategies for improving heterologous protein production from filamentous fungi", Antonie van Leeuwenhoek 65: 245-250, 1994.

Baldari, et al., "A novel leader peptide which allows efficient secretion of a fragment of human interleukin 1β in *Saccharomyces cerevisiae*," *The EMBO Journal*, vol. 6, No. 1, pp. 229-234 (1987).

Baulcombe, "Fast forward genetics based on virus-induced gene silencing," *Curr. Opin. Plant Biology*, vol. 2, pp. 109-113 (1999).

Bechtold et al., "In planta Agrobacterium mediated gene transfer by infiltration of adult *Arabidopsis thaliana* plants", C.R.Acad. Sci. Paris, Sciences de la vie/Life sciences, vol. 316, pp. 1194-1199 (1993).

Becker, et al., Fertile transgenic wheat from microprojectile bombardment of scutellar tissue, *Plant J.*, vol. 5, pp. 299-307 (1994).

Beetham et al., A tool for functional plant genomics: Chimeric RNA/DNA oligonucleotides cause in vivo gene-specific mutations, Proc. Natl. Acad. Sci. USA, vol. 96, pp. 8774-8778, Jul. 1999.

Benowitz et al., "Nicotine intake and dose response when smoking reduced-nicotine content Cigarettes," Clin. Pharmocol. Ther., vol. 80, No. 6, pp. 703-714 (2006). [Abstract].

Boswell, et al., "Specificities of the enzymes of N-alkyltropane biosynthesis in *Brugmansia* and *Datura*," *Phytochemistry*, vol. 52, No. 5, pp. 871-878 (1999). [Abstract].

Boswell, et al., "Metabolism of N-alkyldiamines and N-alkylnortropinones by transformed root cultures of *Nicotiana* and *Brugmansia*", Phytochemistry, vol. 52, No. 5, pp. 855-869 (1999). [Abstract].

Altschul et al., "Gapped BLAST and PSI-BLAST: a new generation of protein database search programs", Nucleic Acids Research, 1997, vol. 23, No. 17, pp. 3389-3402.

Reed, D.G. and Jelesko, J.G., Plant Science (2004) vol. 164, pp. 1123-1130.

Legg, P.D. et al., Journal of Heredity, Jul. 1969; vol. 60, No. 4, p. 213-217.

Foreign Action other than Search Report on CA 2997344 dated Dec. 4, 2020.

Quan, et al., "The Synthesis of Anatabine and Related Compounds", J. Org. Chem., vol. 30, No. 8, pp. 2769-2772 (1965).

Solt, "Nicotine Production and Growth of Excised Tobacco Root", Plant Physiol., vol. 32, No. 5, pp. 480-484 (1957).

\* cited by examiner

Figure 2. RT-PCR analysis of *MPO* expression in different tissues of *N. benthamiana*.

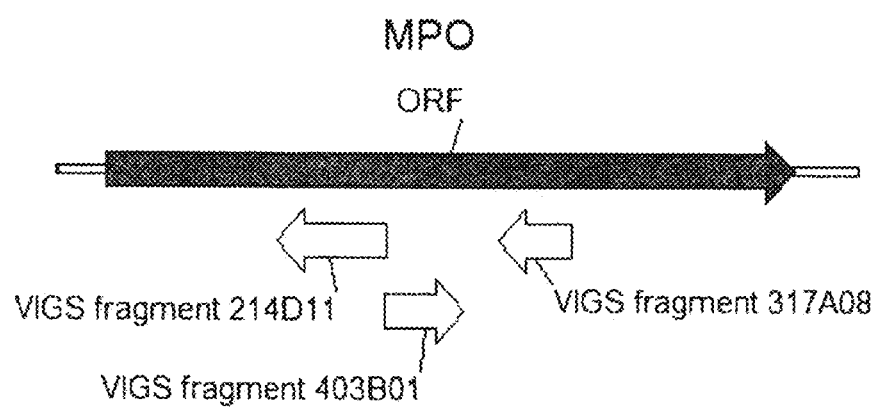
Figure 4. Positions and lengths of MPO gene fragments used for VIGS.

HPLC ANALYSIS OF POLYAMINES IN ROOTS OF TRV-GFP AND TRV-MPO INFECTED PLANTS.

Figure 9. Substrate preference of recombinant MPO enzyme.

Figure 10. Positive-ion electrospray ionization mass spectrometry (ESI-MS) analysis.

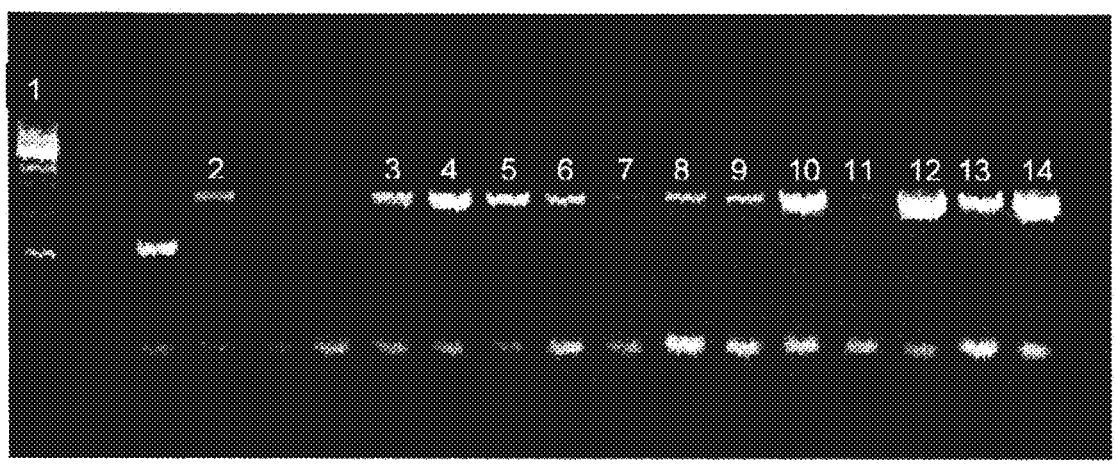
Figure 12. PCR analysis of *N. benthamiana* plants transformed with the MPO gene.

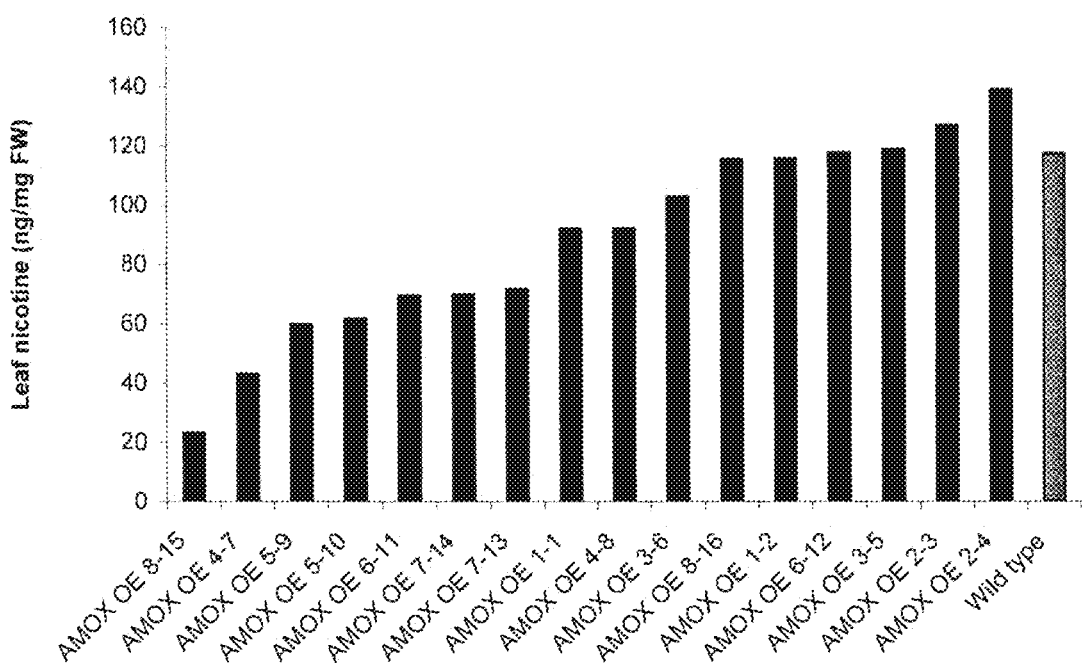
Figure 13. Leaf nicotine levels in stably transformed *N. benthamiana* plants.

SEQUENCE LISTING

<160> NUMBER OF SEQ ID NOS: 20

<210> SEQ ID NO 1
<211> LENGTH: 2763
<212> TYPE: DNA
<213> ORGANISM: Nicotiana sp.

<400> SEQUENCE: 1

```
gaaacaaac  gtacacacac  agtcaagaaa  ctatatactg  acagacatag  tttgaaggga      60
cgctaaaagt  gatttaagtt  ataatcacag  tatatgtcag  tagcctctaa  taatcactgt     120
tggggttctc  atcacagatt  tcttcctagc  taaccagtag  tctcaatggc  cactactaaa     180
cagaaagtga  cggcaccttc  tccttctcct  tctccttctt  cttcgactgc  ttcttgctgt     240
ccttccactt  ccatcctccg  tcgtgaggcg  acagcggcca  tttcagtcgt  gggtgacgga     300
ctgcagaatt  ggacgtccaa  catccctcc   gtcgatgata  aacagaaaaa  gacggcctca     360
tcagctctag  catcattgcc  aaccactgaa  cctctttcct  caaataccctc taccaaaggt     420 atccaaatca  tgacaagggc  tcagacctgc  catcctttgg  accctttatc  tgctgctgag     480
atctcagtgg  ctgtggcaac  tgttagagct  gccggtgaaa  cacctgaggt  cagagatggg     540
atgcgattta  ttgaggtggt  tctggtagaa  ccagataaaa  gtgtagttgc  actggcagat     600
gcatatttct  tcccacctt   tcagtcatca  ttgatgccga  gaaccaaagg  aggatctcat     660
attcctacta  agcttccacc  aaggagagct  aggcttattg  tttacaataa  gaaaacaaat     720
gagacaagca  tatggattgt  tgagctaact  gaagtacatg  ctgctgctcg  aggtggacat     780
cacagaggaa  aagtcatctc  atccaatgtt  gtccctgatg  ttcagccacc  catagatgct     840
caagagtatg  ctgaatgtga  agctgtggtg  aaaagttatc  ctcccttcg   agacgcaatg     900
```

| | |
|---|---:|
| aggagaaggg gtattgatga cttggatctt gtgatggttg acccttggtg tgttggttat | 960 |
| catagtgagg ctgatgctcc tagccgcagg ctcgcgaaac cacttgtatt ctgcaggaca | 1020 |
| gagagtgact gcccaatgga aaatggatat gcaagaccag ttgaaggaat atatgtgctt | 1080 |
| gttgatgtac aaaacatgaa gattatagaa tttgaagacc gaaaacttgt accgttacct | 1140 |
| ccagttgatc cactgaggaa ctacactgct gctgagacaa gaggaggggt tgatcgaagt | 1200 |
| gatgtgaaac tctacatat tattcagccc gagggtccaa gctttcgtat cagtggaaac | 1260 |
| tacgtagagt ggcagaagtg gaattttcgg attggtttca cccctagaga gggtttagtc | 1320 |
| atacactctg tggcgtatct tgatggtagc agaggtcgta gaccaatagc acataggttg | 1380 |
| agttttgtag agatggttgt cccttatggg gatccaaatg atccacatta taggaagaat | 1440 |
| gcatttgatg caggagaaga tggccttgga aagaatgctc attcactgaa gagggggtgt | 1500 |
| gattgtttgg ggtacattaa gtactttgat gcccatttca caaattttac gggaggagtt | 1560 |
| gaaacgactg aaaattgtgt atgcttgcat gaagaagatc acggaatgct ttggaagcat | 1620 |
| caagattgga gaactggcct tgctgaagtt agacggtcta ggcgactaac agtgtctttt | 1680 |
| gtttgtacag tggccaatta tgaatatgca ttctactggc acttctacca ggatggaaaa | 1740 |
| attgaagcgg aagttaaact cactggaatt cttagtttgg gagcattgca acctggagaa | 1800 |
| tatcgcaaat atggtaccac aattttacca ggtttgtatg caccagttca tcaacacttc | 1860 |
| tttgttgcac gaatgaatat ggcagttgat tgtaagccag gagaagcaca caatcaggtt | 1920 |
| gttgaagtaa atgtcaaagt tgaagaacct ggcaaggaaa atgttcataa taatgcattc | 1980 |
| tatgctgaag aaacattgct tagttctgaa ttgcaagcaa tgcgtgactg tgatccgttc | 2040 |
| tctgctcgtc attggattgt taggaacacg agaacggtaa atagaacagg acagctaaca | 2100 |
| gggtacaagc tggtacctgg tccaaactgt ttgccattgg ctggtcctga ggcgaaattt | 2160 |
| ttgagaagag ctgcatttct gaagcacaat ctatgggtta cacaatatgc acctggagaa | 2220 |
| gattttccag gaggagagtt cccaaatcaa aatccccgtg ttggcgaggg attagcttct | 2280 |
| tgggtcaagc aagaccggcc tctgaagaaa agtgatattg ttctctggta tattttggga | 2340 |
| atcacacatg ttcctcggtt ggaagactgg cctgttatgc cagtcgaaca cattggtttt | 2400 |
| gtgctacagc cacatggatt ctttaactgc tccccggctg ttgatgtccc tccgcccttt | 2460 |
| gcttgcgact cagagagcac agacagtgat gttactgaaa ctagtgtagc aaagtccact | 2520 |
| gccactagct tgctggccaa gctttgaatg attatgttat cctaacatga gtcctcctcg | 2580 |
| atcgcctatt tacctacgga taccaaactt ccattttctt ttgatagagt attgaattag | 2640 |
| ttggtgcagg aacattgttt tgattggtct catatatggc acgtttaagc aaagcaagtc | 2700 |
| cctttgtgta ttgatcttga attaagcatg ttataggaa aaaaaaaaa aaaaaaaaa | 2760 |
| aaa | 2763 |

```
<210> SEQ ID NO 2
<211> LENGTH: 2379
<212> TYPE: DNA
<213> ORGANISM: Nicotiana sp.

<400> SEQUENCE: 2
```

| | |
|---|---:|
| atggccacta ctaaacagaa agtgacggca ccttctcctt ctccttctcc ttcttcttcg | 60 |
| actgcttctt gctgtccttc cacttccatc ctccgtcgtg aggcgacagc ggccatttca | 120 |
| gtcgtgggtg acggactgca gaattggacg tccaacatcc cctccgtcga tgataaacag | 180 |

-continued

```
aaaaagacgg cctcatcagc tctagcatca ttgccaacca ctgaacctct ttcctcaaat    240
acctctacca aaggtatcca aatcatgaca agggctcaga cctgccatcc tttggaccct    300
ttatctgctg ctgagatctc agtggctgtg caactgtta gagctgccgg tgaaacacct    360
gaggtcagag atgggatgcg atttattgag gtggttctgg tagaaccaga taaaagtgta    420
gttgcactgg cagatgcata tttcttccca ccttttcagt catcattgat gccgagaacc    480
aaaggaggat ctcatattcc tactaagctt ccaccaagga gagctaggct tattgtttac    540
aataagaaaa caaatgagac aagcatatgg attgttgagc taactgaagt acatgctgct    600
gctcgaggtg gacatcacag aggaaaagtc atctcatcca atgttgtccc tgatgttcag    660
ccacccatag atgctcaaga gtatgctgaa tgtgaagctg tggtgaaaag ttatcctccc    720
tttcgagacg caatgaggag aagggggtatt gatgacttgg atcttgtgat ggttgaccct    780
tggtgtgttg gttatcatag tgaggctgat gctcctagcc gcaggctcgc gaaaccactt    840
gtattctgca ggacagagag tgactgccca atggaaaatg gatatgcaag accagttgaa    900
ggaatatatg tgcttgttga tgtacaaaac atgaagatta tagaatttga agaccgaaaa    960
cttgtaccgt tacctccagt tgatccactg aggaactaca ctgctgctga cagaaggagga   1020 ggggttgatc gaagtgatgt gaaacctcta catattattc agcccgaggg tccaagctt    1080 cgtatcagtg gaaactacgt agagtggcag aagtggaatt ttcggattgg tttcaccct   1140 agagagggtt tagtcataca ctctgtggcg tatcttgatg gtagcagagg tcgtagacca   1200
atagcacata ggttgagttt tgtagagatg gttgtcccctt atgggatcc aaatgatcca   1260 cattatagga agaatgcatt tgatgcagga gaagatggcc ttggaaagaa tgctcattca   1320
ctgaagaggg ggtgtgattg tttggggtac attaagtact ttgatgccca tttcacaaat   1380
tttacgggag gagttgaaac gactgaaaat tgtgtatgct tgcatgaaga agatcacgga   1440
atgctttgga agcatcaaga ttggagaact ggccttgctg aagttagacg gtctaggcga   1500
ctaacagtgt cttttgtttg tacagtggcc aattatgaat atgcattcta ctggcacttc   1560
taccaggatg gaaaaattga agcggaagtt aaactcactg gaattcttag tttgggagca   1620
ttgcaacctg gagaatatcg caaatatggt accacaattt taccaggttt gtatgcacca   1680
gttcatcaac acttctttgt tgcacgaatg aatatggcag ttgattgtaa gccaggagaa   1740
gcacacaatc aggttgttga agtaaatgtc aaagttgaag aacctggcaa ggaaaatgtt   1800
cataataatg cattctatgc tgaagaaaca ttgcttagtt ctgaattgca agcaatgcgt   1860
gactgtgatc cgttctctgc tcgtcattgg attgttagga acacgagaac ggtaaataga   1920
acaggacagc taacagggta caagctggta cctggtccaa actgtttgcc attggctggt   1980
cctgaggcga aatttttgag aagagctgca tttctgaagc acaatctatg ggttacacaa   2040
tatgcacctg gagaagattt tccaggagga gagttcccaa atcaaaatcc ccgtgttggc   2100
gagggattag cttcttgggt caagcaagac cggcctctgg aagaaagtga tattgttctc   2160
tggtatattt ttggaatcac acatgttcct cggttggaag actggcctgt tatgccagtc   2220
gaacacattg gttttgtgct acagccacat ggattcttta actgctcccc ggctgttgat   2280
gtccctccgc cctttgcttg cgactcagag agcacagaca gtgatgttac tgaaactagt   2340
gtagcaaagt ccactgccac tagcttgctg gccaagctt                          2379
```

<210> SEQ ID NO 3
<211> LENGTH: 793
<212> TYPE: PRT
<213> ORGANISM: Nicotiana sp.

<400> SEQUENCE: 3

```
Met Ala Thr Thr Lys Gln Lys Val Thr Ala Pro Ser Pro Ser Pro Ser
1               5                   10                  15

Pro Ser Ser Thr Ala Ser Cys Cys Pro Ser Thr Ser Ile Leu Arg
            20                  25                  30

Arg Glu Ala Thr Ala Ala Ile Ser Val Val Gly Asp Gly Leu Gln Asn
                35                  40                  45

Trp Thr Ser Asn Ile Pro Ser Val Asp Asp Lys Gln Lys Lys Thr Ala
    50                  55                  60

Ser Ser Ala Leu Ala Ser Leu Pro Thr Thr Glu Pro Leu Ser Ser Asn
65              70                  75                  80

Thr Ser Thr Lys Gly Ile Gln Ile Met Thr Arg Ala Gln Thr Cys His
                85                  90                  95

Pro Leu Asp Pro Leu Ser Ala Ala Glu Ile Ser Val Ala Val Ala Thr
            100                 105                 110

Val Arg Ala Ala Gly Glu Thr Pro Glu Val Arg Asp Gly Met Arg Phe
                115                 120                 125

Ile Glu Val Val Leu Val Glu Pro Asp Lys Ser Val Val Ala Leu Ala
130                 135                 140

Asp Ala Tyr Phe Phe Pro Pro Phe Gln Ser Ser Leu Met Pro Arg Thr
145                 150                 155                 160

Lys Gly Gly Ser His Ile Pro Thr Lys Leu Pro Pro Arg Arg Ala Arg
                165                 170                 175

Leu Ile Val Tyr Asn Lys Lys Thr Asn Glu Thr Ser Ile Trp Ile Val
                180                 185                 190

Glu Leu Thr Glu Val His Ala Ala Arg Gly Gly His His Arg Gly
                195                 200                 205

Lys Val Ile Ser Ser Asn Val Val Pro Asp Val Gln Pro Pro Ile Asp
                210                 215                 220

Ala Gln Glu Tyr Ala Glu Cys Glu Ala Val Val Lys Ser Tyr Pro Pro
225                 230                 235                 240

Phe Arg Asp Ala Met Arg Arg Gly Ile Asp Asp Leu Asp Leu Val
                245                 250                 255

Met Val Asp Pro Trp Cys Val Gly Tyr His Ser Glu Ala Asp Ala Pro
                260                 265                 270

Ser Arg Arg Leu Ala Lys Pro Leu Val Phe Cys Arg Thr Glu Ser Asp
                275                 280                 285

Cys Pro Met Glu Asn Gly Tyr Ala Arg Pro Val Glu Gly Ile Tyr Val
290                 295                 300

Leu Val Asp Val Gln Asn Met Lys Ile Ile Glu Phe Glu Asp Arg Lys
305                 310                 315                 320

Leu Val Pro Leu Pro Pro Val Asp Pro Leu Arg Asn Tyr Thr Ala Ala
                325                 330                 335

Glu Thr Arg Gly Gly Val Asp Arg Ser Asp Val Lys Pro Leu His Ile
                340                 345                 350

Ile Gln Pro Glu Gly Pro Ser Phe Arg Ile Ser Gly Asn Tyr Val Glu
                355                 360                 365

Trp Gln Lys Trp Asn Phe Arg Ile Gly Phe Thr Pro Arg Glu Gly Leu
                370                 375                 380

Val Ile His Ser Val Ala Tyr Leu Asp Gly Ser Arg Gly Arg Arg Pro
385                 390                 395                 400

Ile Ala His Arg Leu Ser Phe Val Glu Met Val Val Pro Tyr Gly Asp
```

```
            405                 410                 415
Pro Asn Asp Pro His Tyr Arg Lys Asn Ala Phe Asp Ala Gly Glu Asp
            420                 425                 430

Gly Leu Gly Lys Asn Ala His Ser Leu Lys Arg Gly Cys Asp Cys Leu
        435                 440                 445

Gly Tyr Ile Lys Tyr Phe Asp Ala His Phe Thr Asn Phe Thr Gly Gly
        450                 455                 460

Val Glu Thr Thr Glu Asn Cys Val Cys Leu His Glu Glu Asp His Gly
465                 470                 475                 480

Met Leu Trp Lys His Gln Asp Trp Arg Thr Gly Leu Ala Glu Val Arg
                485                 490                 495

Arg Ser Arg Arg Leu Thr Val Ser Phe Val Cys Thr Val Ala Asn Tyr
            500                 505                 510

Glu Tyr Ala Phe Tyr Trp His Phe Tyr Gln Asp Gly Lys Ile Glu Ala
            515                 520                 525

Glu Val Lys Leu Thr Gly Ile Leu Ser Leu Gly Ala Leu Gln Pro Gly
        530                 535                 540

Glu Tyr Arg Lys Tyr Gly Thr Thr Ile Leu Pro Gly Leu Tyr Ala Pro
545                 550                 555                 560

Val His Gln His Phe Phe Val Ala Arg Met Asn Met Ala Val Asp Cys
                565                 570                 575

Lys Pro Gly Glu Ala His Asn Gln Val Val Glu Val Asn Val Lys Val
            580                 585                 590

Glu Glu Pro Gly Lys Glu Asn Val His Asn Asn Ala Phe Tyr Ala Glu
        595                 600                 605

Glu Thr Leu Leu Ser Ser Glu Leu Gln Ala Met Arg Asp Cys Asp Pro
        610                 615                 620

Phe Ser Ala Arg His Trp Ile Val Arg Asn Thr Arg Thr Val Asn Arg
625                 630                 635                 640

Thr Gly Gln Leu Thr Gly Tyr Lys Leu Val Pro Gly Pro Asn Cys Leu
                645                 650                 655

Pro Leu Ala Gly Pro Glu Ala Lys Phe Leu Arg Arg Ala Ala Phe Leu
            660                 665                 670

Lys His Asn Leu Trp Val Thr Gln Tyr Ala Pro Gly Glu Asp Phe Pro
        675                 680                 685

Gly Gly Glu Phe Pro Asn Gln Asn Pro Arg Val Gly Glu Gly Leu Ala
        690                 695                 700

Ser Trp Val Lys Gln Asp Arg Pro Leu Glu Glu Ser Asp Ile Val Leu
705                 710                 715                 720

Trp Tyr Ile Phe Gly Ile Thr His Val Pro Arg Leu Glu Asp Trp Pro
                725                 730                 735

Val Met Pro Val Glu His Ile Gly Phe Val Leu Gln Pro His Gly Phe
            740                 745                 750

Phe Asn Cys Ser Pro Ala Val Asp Val Pro Pro Phe Ala Cys Asp
        755                 760                 765

Ser Glu Ser Thr Asp Ser Asp Val Thr Glu Thr Ser Val Ala Lys Ser
        770                 775                 780

Thr Ala Thr Ser Leu Leu Ala Lys Leu
785                 790

<210> SEQ ID NO 4
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 4 ttttttttttt tttttttttt ttttt                                         25

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgggatcctc gagcggccgc ccgggcaggt                                     30

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggaattcag cgtggtcgcg gccgaggt                                       28

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gttactcaag gaagcacgat gag                                            23

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagtcgagaa tgtcaatctc gtag                                           24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cttgagcatc tatgggtggc                                                20

<210> SEQ ID NO 10
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 10
agcaatgcgt gactgtgatc cg                                              22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctacaatgag cttcgtgttg c                                               21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgctgaggga agccaagata                                                 20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcatgctctt tgagtcagca a                                               21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caccagtgtt cattgttcac t                                               21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aggtggacat cacagaggaa                                                 20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
                  primer

<400> SEQUENCE: 16
agtcgtttca actcctcccg ta                                                    22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atggccacta ctaaacagaa ag                                                    22

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tagtttagcg gccgctcaaa gcttggccag caagct                                     36

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
actcctcccg taaaatttgt ga                                                    22

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcggccgcac tagtgatatc                                                       20
```

NUCLEIC ACID ENCODING N-METHYLPUTRESCINE OXIDASE AND USES THEREOF

CROSS-REFERENCE TO RELATED APPLICATIONS

This application is a continuation of U.S. patent application Ser. No. 16/877,401, filed May 18, 2020, which is a continuation of U.S. patent application Ser. No. 16/054,711, filed Aug. 3, 2018, now U.S. Pat. No. 10,689,658, which is a continuation of U.S. patent application Ser. No. 15/242,129, filed Aug. 19, 2016, now U.S. Pat. No. 10,041,084, which is a divisional of U.S. patent application Ser. No. 13/774,902, filed Feb. 22, 2013, now U.S. Pat. No. 9,422,532, which is a divisional of U.S. patent application Ser. No. 12/305,483, filed Feb. 12, 2009, now U.S. Pat. No. 8,410,341, which is the U.S. National Phase of International Patent Application No. PCT/IB2007/003550, filed Jun. 19, 2007, which claims the benefit of priority from U.S. Provisional Patent Application Nos. 60/814,542, filed Jun. 19, 2006, and 60/901,654, filed Feb. 16, 2007. The contents of these applications are incorporated herein by reference in their entirety.

FIELD OF THE INVENTION

The present invention relates to molecular biology and alkaloid biosynthesis in plants, plant cells or other cells. The invention relates, inter alia, to nucleic acid sequences that encode N-methylputrescine oxidase (MPO) and to methods for their use in modifying alkaloid production in plants, particularly but not exclusively nicotinic alkaloid production in a tobacco plant, and for producing alkaloid biosynthetic enzymes in plant cells or other cells.

BACKGROUND OF THE INVENTION

Pyrrolidine alkaloids (e.g., nicotine) and tropane alkaloids (e.g., scopolamine and cocaine) are plant natural products that exhibit a diverse range of pharmacological activities. For example, nicotine may have utility for increasing cognitive function and is used in nicotine replacement therapy for smoking cessation. Tropane alkaloids are important anticholinergic drugs. Cocaine is used as a local anesthetic. These compounds are all isolated from plant sources for use as pharmaceutical drugs.

It would be of interest to enhance the production of pyrrolidine and tropane alkaloids in plants or plant cells by genetic engineering for the more efficient commercial production of these compounds for the pharmaceutical industry. Enhanced production of pyrrolidine and tropane alkaloids could be accomplished through selective breeding or genetic engineering using genes that encode enzymes in the biosynthetic pathways leading to these alkaloids. Genetic engineering for the accumulation of pathway intermediates, or reduction of end-product alkaloid levels, could be accomplished through classical or targeted mutagenesis approaches, such as Targeting Induced Local Lesions in Genomes (TILLING), or the specific silencing of genes encoding these enzymes via RNA interference and related techniques.

It would also be of interest to block the biosynthetic pathways leading to the production of these alkaloids at defined metabolic steps. The purpose of this would be to accumulate metabolic intermediates that may be of high value themselves or to generate plants that contain modified or reduced levels of end-product alkaloids. Tobacco plants that are genetically engineered to contain reduced nicotine levels may be useful for the production of plant-made pharmaceuticals, reduced-nicotine or nicotine-free cigarettes for use as smoking cessation aids (Benowitz et al. Clin Pharmocol Ther. 80(6):703-14 (2006)) and for use as low-toxicity industrial, food or biomass crops.

There are few genes known that encode enzymes involved in pyrrolidine or tropane alkaloid biosynthesis. This limits the ability to genetically engineer the pathways leading to these useful molecules.

An example of a known gene that encodes an enzyme involved in pyrrolidine alkaloid biosynthesis is the quinolate phosphoribosyl transferase (QPT) gene which has been cloned from *N. tabacum* and *N. rustica*; see U.S. Pat. Nos. 6,423,520 and 6,586,661, and Sinclair et al., *Plant Mol. Biol.* 44: 603-17 (2000). QPT suppression provides significant nicotinic alkaloid reductions in transgenic tobacco plants. Xie et al., *Recent Advances in Tobacco Science* 30: 17-37 (2004).

U.S. Pat. Nos. 5,369,023 and 5,260,205 discuss decreasing nicotine levels by suppressing putrescine N-methyltransferase (PMT) sequence. Suppression of an endogenous putrescine N-methyltransferase (PMT) sequence has been shown to reduce nicotine levels and increase anatabine levels by about 2-to-6-fold. Hibi et al., *Plant Cell* 6: 723-35 (1994); Sato et al. *Proc Natl Acad Sci USA* 98:367-72 (2001); Chintapakorn and Hamill, *Plant Mol. Biol.* 53:87-105 (2003); Steppuhn et al., *PLoS Biol.* 2:8: e217: 1074-1080 (2004). Overexpression of *Nicotiana tabacum* PMT in *N. sylvestris* resulted in an increase in nicotine content (Sato et al. *Proc Natl Acad Sci USA* 98:367-72 (2001)).

Suppression of endogenous A622 and NBB1 sequences has been shown to reduce nicotinic alkaloid levels in tobacco plants; see International patent publication WO 2006/109197. A gene encoding a cytochrome P450 monooxygenase that converts nicotine to nornicotine has been cloned from *N. tabacum*. Siminszky B., et al., *Proc Natl Acad Sci USA* 102:14919-24, (2005); Gavilano et al. *J. Agric. Food Chem.* 54, 9071-9078 (2006).

The enzymatic activity of MPO was first detected in tobacco roots over three decades ago, Mizusaki S et al., *Phytochemistry* 11: 2757-2762 (1972), but the gene encoding this enzyme has remained unidentified until the present invention.

MPO plays a role in the pathway for the biosynthesis of alkaloids in plants, including medicinal tropane alkaloids. Hashimoto and Yamada, *Annu. Rev. Plant Physiol. Plant Mol. Biol.* 45: 257-285 (1994); Kutchan, In: Cordell, G. A. (ed.) ALKALOIDS (San Diego), vol. 50. Academic Press, Inc., San Diego, CA, USA, (1998) pp. 257-316.

MPO enzymes have been purified from the roots of *N. tabacum* and *N. rustica, Hyoscyamus niger*, and *Brugmansia candida* x *aurea* hybrid and were shown to oxidize N-methylputrescine more efficiently than putrescine and cadaverine. Mizusaki et al., *Phytochemistry* 11: 2757-2762 (1972); Feth and Wagner, *Phytochemistry* 24: 1653-1655 (1985); Davies et al., *Phytochemistry* 28: 1573-1578 (1989); Hashimoto et al. *Plant Physiol.* 93:216-221 (1990); Walton and McLauchlan, *Phytochemistry* 29: 1455-1457 (1990); Haslam and Young, *Phytochemistry* 3 1: 4075-4079 (1992); McLauchlan et al., *Planta* 19: 440-445 (1993); Boswell et al., *Phytochemistry* 52: 871-878 (1999).

Anabasine and anatalline contain a piperidine moiety. The piperidine moiety of anabasine is thought to be derived from cadaverine via delta-1-piperidine in tobacco. Watson and Brown, *J. Chem. Soc. Perkin Trans.* 1: 2607-2610 (1990). Cadaverine is a good substrate for general diamine oxidases but is also a substrate for MPO, although it has a lower affinity than N-methylated diamines. Hashimoto et al. (1990), supra; Walton and McLauchlan, *Phytochemistry* 29: 1455-1457 (1990); Boswell et al., *Phytochemistry* 52: 871-878 (1999).

Katoh et al., *Plant Cell Physiol.* 48(3): 550-554 (2007), and Heim et al., *Phytochemistry* 68:454-463 (2007), both of which published after the filing of U.S. provisional application Ser. No. 60/814,542, disclose genes from tobacco that encode N-methylputrescine oxidase (MPO), which is involved in the nicotine biosynthetic pathway. There is no teaching of any method or use involving this gene for modifying nicotine production in plants, or for modifying production of any other alkaloid in plants.

Accordingly, there is a continuing need to identify additional genes whose expression can be regulated to decrease or increase the biosynthesis of alkaloids or to alter a plant's alkaloid profile by regulating the biosynthesis of a specific alkaloid(s).

SUMMARY OF THE INVENTION

In one aspect, the invention provides an isolated nucleic acid molecule comprising a nucleotide sequence selected from the group consisting of: (a) a nucleotide sequence set forth in SEQ ID NO: 1; (b) a nucleotide sequence set forth in SEQ ID NO: 2; (c) a nucleotide sequence that encodes a polypeptide having the amino acid sequence set forth in SEQ ID NO: 3; (d) a nucleotide sequence that is at least 85% identical to the nucleotide sequences of (a), (b), or (c) and encodes an MPO enzyme; (e) a nucleotide sequence that hybridizes under stringent conditions to the nucleotide sequences of (a), (b), (c), or (d) and encodes an MPO enzyme; and (f) a nucleotide sequence that differs from the nucleic acid sequence of (a) or (b) due to the degeneracy of the genetic code and encodes an MPO enzyme.

In another aspect, the invention provides a method of producing MPO enzyme, comprising (a) genetically engineering a cell with a nucleic acid construct comprising the isolated nucleic acid molecule of claim 1; and (b) growing the engineered cell under conditions such that MPO is produced.

In another aspect, the invention provides a recombinant MPO enzyme having the amino acid sequence of SEQ ID NO: 3 or a variant of SEQ ID NO: 3.

In one embodiment, a genetically engineered host cell comprises the nucleic acid sequence. In a further embodiment, the host cell is selected from the group consisting of bacteria, yeast, filamentous fungi, algae, green plants, and mammalian cells. In another embodiment, a plant comprises the host cell.

In another aspect, the invention provides a method for reducing an alkaloid in a plant, comprising down-regulating N-methylputrescine oxidase expression relative to a control plant. In one embodiment, the alkaloid is a pyrrolidine alkaloid. In a further embodiment, the pyrrolidine alkaloid is nicotine. In another embodiment, the plant belongs to genus *Nicotiana*. In another embodiment, the plant is *Nicotiana tabacum*. In another embodiment, N-methylputrescine oxidase expression is down-regulated by (a) introducing into the plant a nucleotide sequence comprising i) at least 21 consecutive nucleotides of SEQ ID NO: 1, wherein said consecutive nucleotides are in either sense or antisense orientation; and (b) growing the plant under conditions whereby said nucleotide sequence decreases levels of N-methylputrescine oxidase in the plant compared to a control plant grown under similar conditions. In one embodiment, the conditions induce co-suppression of an endogenous MPO gene.

In another aspect, the invention provides a method for reducing a pyrrolidine alkaloid in a plant, comprising down-regulating MPO and at least one of NBB1, A622, QPT and PMT.

In another aspect, the invention provides a method for decreasing pyrrolidine alkaloid levels in a population of plants, comprising (a) providing a population of mutated plants; (b) detecting a target mutated plant within said population, wherein said target mutated plant has decreased expression of N-methylputrescine oxidase gene or decreased activity of N-methylputrescine oxidase enzyme compared to a control plant provided under similar conditions, said detecting comprising using primers developed from SEQ ID NO: 1 or SEQ ID NO: 2 to PCR amplify regions of the N-methylputrescine oxidase gene from mutated plants in the population of mutated plants, identifying mismatches between the amplified regions and corresponding regions in wild-type gene that lead to the decreased expression of N-methylputrescine oxidase gene or decreased activity of N-methylputrescine oxidase enzyme, and identifying the mutated plant that contains the mismatches; and (c) selectively breeding the target mutated plant to produce a population of plants having decreased expression of N-methylputrescine oxidase gene or decreased activity of N-methylputrescine oxidase enzyme compared to a population of control plants produced under similar conditions.

In one embodiment, the pyrrolidine alkaloid is nicotine. In another embodiment, the plant is *Nicotiana tabacum*.

In another aspect, the invention provides a host cell genetically engineered with a nucleotide sequence comprising at least 21 consecutive nucleotides of SEQ ID NO: 1, wherein said consecutive nucleotides are in either sense or antisense orientation. In one embodiment, the cell is a cell of a plant from a member of family Solanaceae or family Erythroxylaceae. In another embodiment, the cell is a cell of a plant from a member of genus *Nicotiana, Datura, Atropa, Duboisia, Hyoscyamus, Mandragora, Brugmansia, Scopolia* or *Erythroxylon*. In another embodiment, the cell is a cell of a plant from a member of the *Nicotiana* genus. In another embodiment, the cell is a cell of a plant of the species *Nicotiana tabacum*. In a further embodiment, the nucleotide sequence comprises SEQ ID NO: 1 or SEQ ID NO: 2.

In another embodiment, there is provided a reduced alkaloid plant produced by any of the preceding methods. In another embodiment, the reduced alkaloid is nicotine. In a further embodiment, a reduced alkaloid product is produced from the reduced alkaloid plant. In another embodiment, the reduced alkaloid is nicotine.

In another aspect, the invention provides a method of increasing MPO enzyme in a plant comprising (a) introducing into the plant a nucleic acid construct comprising a nucleotide sequence encoding an MPO enzyme; and (b) growing the plant under conditions whereby the nucleotide sequence is expressed thereby increasing levels of MPO enzyme in the plant compared to a control plant grown under similar conditions.

In one embodiment, the plant is a member of family Solanaceae or family Erythroxylaceae. In another embodiment, the plant is a member of genus *Nicotiana, Datura, Atropa, Duboisia, Hyoscyamus, Mandragora, Brugmansia, Scopolia* or *Erythroxylon*. In another embodiment, the level of a tropane alkaloid level is increased, and said tropane alkaloid comprises cocaine or scopolamine.

In another aspect, the invention provides a method of increasing pyrrolidine alkaloid levels in a plant, comprising (a) introducing into the plant a nucleotide sequence encoding an MPO enzyme and a nucleotide sequence encoding at least one enzyme selected from the group consisting of NBB1, A622, QPT and PMT; and (b) growing the plant under conditions whereby the plant produces increased levels of N-methylputrescine oxidase and at least one enzyme selected from the group consisting of NBB1, A622, QPT and PMT compared to a control plant grown under similar conditions.

In one embodiment, the invention provides an increased alkaloid plant produced by any of the preceding methods.

BRIEF DESCRIPTION OF THE DRAWINGS

FIG. 4 depicts positions and lengths of MPO gene fragments used for VIGS silencing of nicotine production in *N. benthamiana* plants relative to the full-length MPO cDNA.

FIG. 12 depicts gel electrophoresis analysis of PCR amplicons from plants transformed with an MPO overexpression construct.

FIG. 13 depicts leaf nicotine levels in wild-type and transgenic plants overexpressing MPO.

DETAILED DESCRIPTION OF THE INVENTION

The present inventors have cloned a gene encoding N-methylputrescine oxidase (MPO). The nucleic acid sequence of the MPO gene, SEQ ID NO: 1, has been determined. The open reading frame (ORF) of SEQ ID NO: 1, set forth in SEQ ID NO: 2, encodes the polypeptide sequence set forth in SEQ ID NO: 3.

Figure 1:
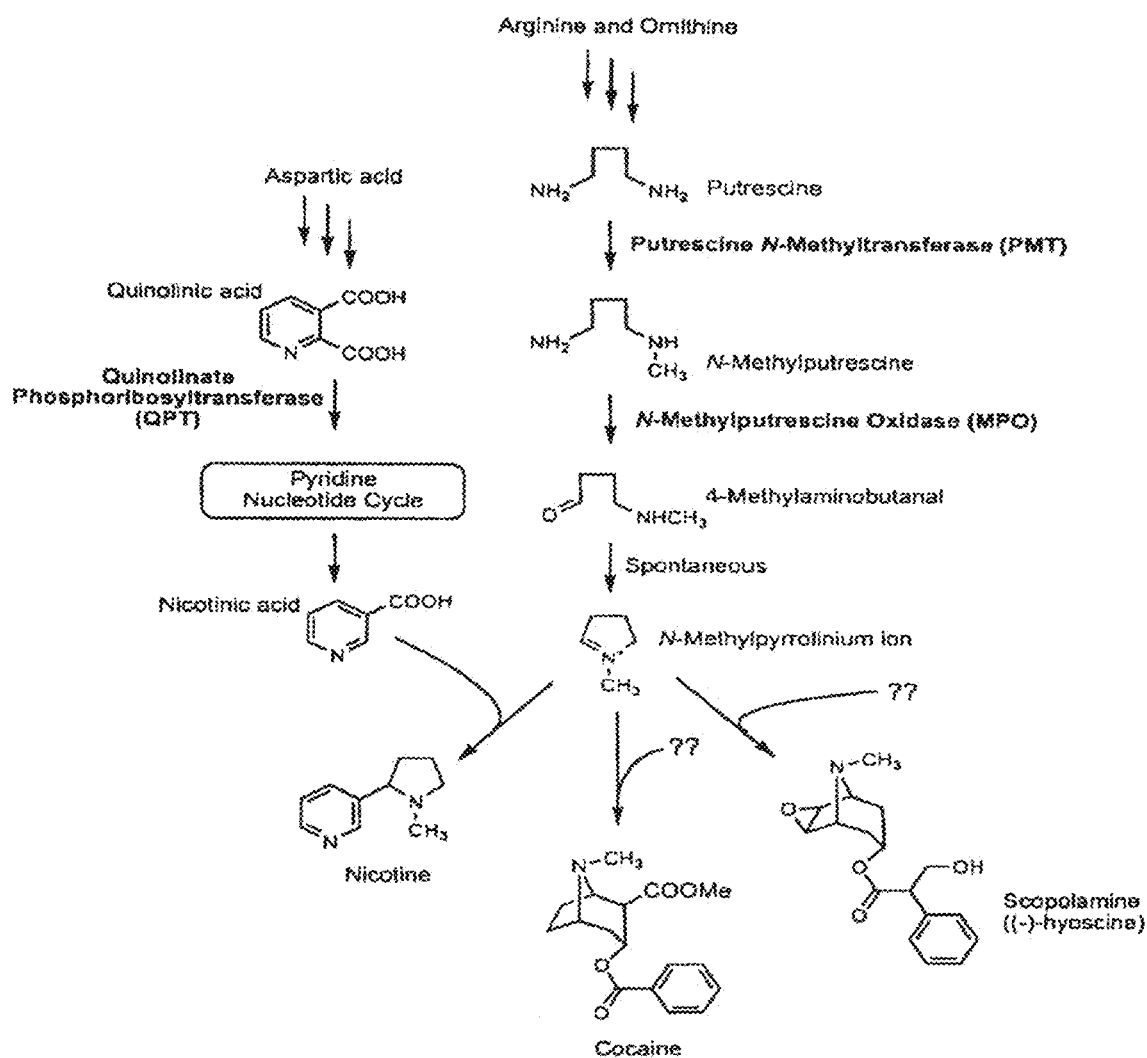
FIG. 1 depicts proposed biosynthetic pathways leading to the pyrrolidine alkaloid, nicotine, and the tropane alkaloids, cocaine and scopolamine.

With reference to FIG. 1, the biosynthesis of both pyrrolidine alkaloids (e.g., nicotine) and tropane alkaloids (e.g., cocaine and scopolamine) involves N-methylpyrrolinium ion as a metabolic intermediate. It is apparent that the production of these alkaloids can be modulated by affecting the enzymes and/or intermediates within these pathways.

MPO catalyzes the oxidative deamination of N-methylputrescine to form 4-methylaminobutanal, which spontaneously cyclizes to yield N-methylpyrrolinium ion. N-methylpyrrolinium ion is a key building block for valuable alkaloids. FIG. 1 shows the structure of the key metabolic intermediate, N-methylpyrrolinium ion, as well as its positions in the structures of nicotine, cocaine, and scopolamine. The two known enzymes, quinolinate phosphoribosyl transferase (QPT) and putrescine N-methyltransferase (PMT), also are indicated.

Assuming there are sufficient levels of N-methylputrescine available, it is apparent from FIG. 1 that increasing MPO levels and/or activity will increase N-methylpyrrolinium ion levels, which in turn will result in the production of more nicotine, cocaine and/or scopolamine. Alternatively, nicotine, cocaine and/or scopolamine biosynthesis will be decreased if MPO levels and/or activity are reduced sufficiently.

The MPO gene or fragments thereof may be used to suppress pyrrolidine alkaloid biosynthesis (e.g., of nicotine) in plants that naturally produce the pyrrolidine alkaloids. For example, *Nicotiana* spp. (e.g. *N. tabacum*, *N. rustica* and *N. benthamiana*) naturally produce nicotine. *N. tabacum* remains an agricultural crop of high value and biotechnological uses of this plant continue to increase. Blocking nicotine biosynthesis by MPO suppression leads to creating tobacco varieties that contain zero or low nicotine levels for use as low-toxicity production platforms for the production of plant-made pharmaceuticals (PMPs) (e.g. recombinant proteins and antibodies) or as industrial, food and biomass crops.

Definitions

All technical terms employed in this specification are commonly used in biochemistry, molecular biology and agriculture; hence, they are understood by those skilled in the field to which this invention belongs. Those technical terms can be found, for example in: MOLECULAR CLONING: A LABORATORY MANUAL 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (including periodic updates); SHORT PROTOCOLS IN MOLECULAR BIOLOGY: A COMPENDIUM OF METHODS FROM CURRENT PROTOCOLS IN MOLECULAR BIOLOGY 5th ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997. Methodology involving plant biology techniques are described here and also are described in detail in treatises such as METHODS IN PLANT MOLECULAR BIOLOGY: A LABORATORY COURSE MANUAL, ed. Maliga et al., Cold Spring Harbor Laboratory Press, Cold Spring Harbor, N.Y., 1995.

The terms "encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein.

As used herein, "expression" denotes the production of an RNA product through transcription of a gene or the production of the protein product encoded by a nucleotide sequence.

Overexpression" or "up-regulation" is used to indicate that expression of a particular gene sequence or variant thereof, in a cell or plant, including all progeny plants derived thereof, has been increased by genetic engineering, relative to a control cell or plant (e.g., "MPO overexpression").

The terms "suppression" or "down-regulation" are used synonymously to indicate that expression of a particular gene sequence variant thereof, in a cell or plant, including all progeny plants derived thereof, has been reduced by genetic engineering, relative to a control cell or plant (e.g., "MPO down-regulation").

An "alkaloid" is a nitrogen-containing basic compound found in plants and produced by secondary metabolism. A "pyrrolidine alkaloid" is an alkaloid containing a pyrrolidine ring as part of its molecular structure, for example, nicotine. Nicotine and related alkaloids are also referred to as pyridine alkaloids in the published literature. A "pyridine alkaloid" is an alkaloid containing a pyridine ring as part of its molecular structure, for example, nicotine. A "tropane alkaloid" is an alkaloid containing a bicyclic tropane ring system as part of its molecular structure for example, scopolamine or cocaine. A "nicotinic alkaloid" is nicotine or an alkaloid that is structurally related to nicotine and that is synthesized from a compound produced in the nicotine biosynthesis pathway. Illustrative nicotinic alkaloids include but are not limited to nicotine, nornicotine, anatabine, anabasine, anatalline, N-methylanatabine, N-methylanabasine, myosmine, anabaseine, formylnornicotine, nicotyrine, and cotinine. Other very minor nicotinic alkaloids in tobacco leaf are reported, for example, in Hecht, S. S. et al., *Accounts of Chemical Research* 12: 92-98 (1979); Tso, T. C., Production, Physiology and Biochemistry of Tobacco Plant. Ideals Inc., Beltsville, MD (1990).

As used herein "alkaloid content" means the total amount of alkaloids found in a plant, for example, in terms of pg/g dry weight (DW) or ng/mg fresh weight (FW). "Nicotine content" means the total amount of nicotine found in a plant, for example, in terms of mg/g DW or FW.

"Decreased nicotine tobacco plant" or "reduced nicotine tobacco plant" encompasses a genetically engineered tobacco plant that has a decrease in nicotine content to a level less than 50%, and preferably less than 10%, or 1% of the nicotine content of a control plant of the same species or variety.

"Increased nicotine tobacco plant" encompasses a genetically engineered plant that has an increase in nicotine content greater than 10%, and preferably greater than 50%, 100%, or 200% of the nicotine content of a control plant of the same species or variety.

"MPO activity" is the enzymatic oxidation of N-methylputrescine to form 4-methylaminobutanal and hydrogen peroxide catalyzed by the enzyme N-methylputrescine oxidase.

An "N-methylputrescine oxidase," "MPO" or "MPO enzyme" is an enzyme that oxidases N-methylputrescine to form N-methylaminobutanal.

I. Reducing Alkaloid Production in Plants

A. Decreasing Alkaloids by Suppressing MPO.

Alkaloid (e.g. nicotine) production may be reduced by suppression of endogenous MPO genes using the MPO sequence of the present invention in a number of ways generally known in the art, for example, RNA interference (RNAi) techniques, artificial microRNA techniques, virus-induced gene silencing (VIGS) techniques, antisense techniques, sense co-suppression techniques and targeted mutagenesis techniques. Accordingly, the present invention provides methodology and constructs for decreasing alkaloid content in a plant, by suppressing an MPO gene. Suppressing more than one MPO gene may further decrease alkaloids levels in a plant.

B. Decreasing Alkaloids by Suppressing MPO and at Least One of A622, NBB1, QPT, and PMT.

Previous reports indicate that suppressing more than one alkaloid biosynthesis gene in *Nicotiana* decreases nicotinic alkaloid content further than suppressing only one. For example, suppressing both A622 and N881 further reduces nicotine levels than suppressing either A622 or N881. WO/2006/109197. Accordingly, the present invention contemplates further decreasing alkaloid content by suppressing MPO and one or more of A622, N881, QPT, and PMT. Pursuant to this aspect of the invention, a nucleic acid construct comprising MPO and one or more of A622, N881, QPT, and PMT is introduced into a cell or plant. An illustrative nucleic acid construct may comprise both MPO and QPT.

II. Increasing Alkaloid Production in Plants

A. Increasing Alkaloids by Overexpressing MPO.

The present invention also relates to increasing alkaloids in plants by overexpressing MPO. The MPO gene or its open reading frame may be used to engineer overproduction of pharmaceutical alkaloids, for example pyrrolidine alkaloids (e.g. nicotine) and/or tropane alkaloids (e.g. scopolamine and cocaine), in plants.

B. Increasing Alkaloids by Overexpressing MPO and at Least One of PMT, QPT, A622 and NBB1.

WO 2005/018307 discusses methods by which alkaloids, such as nicotine, can be further increased by overexpressing more than one gene in the alkaloid biosynthesis pathway. Sato, F., et al. Metabolic engineering of plant alkaloid biosynthesis. Proc Natl Acad Sci USA. 98(1):367-72 (2001). Therefore, the present invention contemplates that overexpressing MPO and at least one additional gene in the alkaloid biosynthesis pathway, such as PMT, will result in greater alkaloid production than up-regulating MPO alone.

Pursuant to this aspect of the invention, a nucleic acid construct comprising MPO and at least one of A622, N881, QPT, and PMT is introduced into a plant cell. An illustrative nucleic acid construct may comprise, for example, both MPO and PMT. Similarly, for example, a genetically engineered plant overexpressing MPO and PMT may be produced by crossing a transgenic plant overexpressing MPO with a transgenic plant overexpressing PMT. Following successive rounds of crossing and selection, a genetically engineered plant overexpressing MPO and PMT can be selected.

III. Producing MPO Enzyme

MPO can be introduced into a host cell, thereby producing MPO enzyme in an organism or cell that does not produce this enzyme otherwise. A variety of products can be produced from these engineered organisms and cells, including alkaloids, alkaloid precursors, alkaloid analogs, and alkaloid biosynthesis enzymes. These products may include nicotine, nicotine precursors, nicotine analogs, and nicotine biosynthesis enzymes. Since MPO catalyzes a key step in the pathway leading to tropane alkaloids (e.g. scopolamine and cocaine), cells containing an introduced MPO gene can also be used to produce tropane alkaloids, tropane alkaloid precursors, tropane analogs, and tropane biosynthetic enzymes. Illustrative host cells include but are not limited to green plant cells, bacteria, yeast, filamentous fungi, algae, and mammalian cells.

Alkaloid Biosynthesis Sequences

Alkaloid biosynthesis genes have been identified in several plant species, exemplified by *Nicotiana* plants. Accordingly, the present invention embraces any nucleic acid, gene, polynucleotide, DNA, RNA, mRNA, or cDNA molecule that is isolated from the genome of a plant species, or produced synthetically, that increases alkaloid biosynthesis. Additionally, expression of such alkaloid biosynthesis sequence produces alkaloids in a cell, such as an insect cell. The DNA or RNA may be double-stranded or single-stranded. Single-stranded DNA may be the coding strand, also known as the sense strand, or it may be the non-coding strand, also called the anti-sense strand.

It is understood to one skilled in the art that MPO of the present invention includes the sequences set forth in SEQ ID NO: 1 and SEQ ID NO: 2, including fragments thereof at least about 21 consecutive nucleotides, which are of a sufficient length as to be useful induction of gene silencing in plants (Hamilton, A J and Baulcombe, D C Science 286, 950-952 (1999)). The invention includes as well as nucleic acid molecules comprised of "variants" of SEQ ID NO: 1 and SEQ ID NO: 2, with one or more bases deleted, substituted, inserted, or added, which variant codes for a polypeptide with alkaloid biosynthesis activity. Accordingly, sequences having "base sequences with one or more bases deleted, substituted, inserted, or added" retain physiological activity even when the encoded amino acid sequence has one or more amino acids substituted, deleted, inserted, or added. Additionally, multiple forms of MPO may exist, which may be due to post-translational modification of a gene product, or to multiple forms of the MPO gene. Nucleotide sequences that have such modifications and that code for an alkaloid biosynthesis enzyme are included within the scope of the present invention.

For example, the poly A tail or 5'- or 3'-end, nontranslated regions may be deleted, and bases may be deleted to the extent that amino acids are deleted. Bases may also be substituted, as long as no frame shift results. Bases also may be "added" to the extent that amino acids are added. It is essential, however, that any such modification does not result in the loss of alkaloid biosynthesis enzyme activity. A modified DNA in this context can be obtained by modifying the DNA base sequences of the invention so that amino acids at specific sites are substituted, deleted, inserted, or added by site-specific mutagenesis, for example. Zoller & Smith, *Nucleic Acid Res.* 10: 6487-500 (1982).

An alkaloid biosynthesis sequence can be synthesized ab initio from the appropriate bases, for example, by using an appropriate protein sequence disclosed herein as a guide to create a DNA molecule that, though different from the native DNA sequence, results in the production of a protein with the same or similar amino acid sequence. This type of synthetic DNA molecule is useful when introducing a DNA sequence into a non-plant cell, coding for a heterologous protein, that reflects different (non-plant) codon usage frequencies and, if used unmodified, can result in inefficient translation by the host cell.

By "isolated" nucleic acid molecule(s) is intended a nucleic acid molecule, DNA or RNA, which has been removed from its native environment. For example, recombinant DNA molecules contained in a DNA construct are considered isolated for the purposes of the present invention. Further examples of isolated DNA molecules include recombinant DNA molecules maintained in heterologous host cells or DNA molecules that are purified, partially or substantially, in solution. Isolated RNA molecules include in vitro RNA transcripts of the DNA molecules of the present invention. Isolated nucleic acid molecules, according to the present invention, further include such molecules produced synthetically.

A "chimeric nucleic acid" comprises a coding sequence or fragment thereof linked to a nucleotide sequence that is different from the nucleotide sequence with which it is associated in cells in which the coding sequence occurs naturally.

"Heterologous nucleic acid" refers to a nucleic acid, DNA or RNA, which has been introduced into a cell (or the cell's ancestor) which is not a copy of a sequence naturally found in the cell into which it is introduced. Such heterologous nucleic acid may comprise segments that are a copy of a sequence which is naturally found in the cell into which it has been introduced, or fragments thereof.

"Endogenous nucleic acid" or "endogenous sequence" is "native" to, i.e., indigenous to, the plant or organism that is to be genetically engineered. It refers to a nucleic acid, gene, polynucleotide, DNA, RNA, mRNA, or cDNA molecule that is present in the genome of a plant or organism that is to be genetically engineered.

"Exogenous nucleic acid" refers to a nucleic acid, DNA or RNA, which has been introduced into a cell (or the cell's ancestor) through the efforts of humans. Such exogenous nucleic acid may be a copy of a sequence which is naturally found in the cell into which it was introduced, or fragments thereof.

Unless otherwise indicated, all nucleotide sequences determined by sequencing a DNA molecule herein were determined using an automated DNA sequencer, such as the Model 3730xl from Applied Biosystems, Inc. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

For the purpose of the invention, two sequences hybridize when they form a double-stranded complex in a hybridization solution of 6×SSC, 0.5% SDS, 5×Denhardt's solution and 100 µg of non-specific carrier DNA. See Ausubel et al., supra, at section 2.9, supplement 27 (1994). Sequences may hybridize at "moderate stringency," which is defined as a temperature of 60° C. in a hybridization solution of 6×SSC, 0.5% SDS, 5×Denhardt's solution and 100 µg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 h. For high stringency, the wash temperature is increased to 68° C. For the purpose of the invention, hybridized nucleotides are those that are detected using 1 ng of a radiolabeled probe having a specific radioactivity of 10,000 cpm/ng, where the hybridized nucleotides are clearly visible following exposure to X-ray film at −70° C. for no more than 72 hours.

"Sequence identity" or "identity" in the context of two polynucleotide (nucleic acid) or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties, such as charge and hydrophobicity, and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers & Miller, *Computer Applic. Biol. Sci.* 4: 11-17 (1988), as implemented in the program PC/GENE (Intelligenetics, Mountain View, California, USA).

Use in this description of a percentage of sequence identity denotes a value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The present application is directed to such nucleic acid molecules which are at least 60%, 65%, 70%, 75%, 80%, 85%, 90%, 95%, 96%, 97%, 98%, 99% or 100% identical to a nucleic acid sequence described in any of SEQ ID NO: 1-2. Preferred are nucleic acid molecules which are at least 95%, 96%, 97%, 98%, 99% or 100% identical to the nucleic acid sequence shown in any of SEQ ID NO: 1-2. Differences between two nucleic acid sequences may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 85%, 90%, 95%, 96%, 97%, 98% or 99% identical to a reference nucleotide sequence refers to a comparison made between two molecules using standard algorithms well known in the art and can be determined conventionally using publicly available computer programs such as the BLASTN algorithm. See Altschul et al., *Nucleic Acids Res.* 25: 3389-402 (1997).

The present invention further provides nucleic acid molecules comprising the nucleotide sequence of SEQ ID NO: 1 and SEQ ID NO: 2, which encode an active alkaloid biosynthesis enzyme, wherein the enzyme has amino acid sequence that corresponds to SEQ ID NO: 3, and wherein the protein of the invention encompasses amino acid substitutions, additions and deletions that do not alter the function of the alkaloid biosynthesis enzyme.

A "variant" is a nucleotide or amino acid sequence that deviates from the standard, or given, nucleotide or amino acid sequence of a particular gene or protein. The terms "isoform," "isotype," and "analog" also refer to "variant" forms of a nucleotide or an amino acid sequence. An amino acid sequence that is altered by the addition, removal, or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. "Variant" may also refer to a "shuffled gene" such as those described in Maxygen-assigned patents (e.g. U.S. Pat. No. 6,602,986).

Methodology for Reducing Alkaloids

In one aspect of the invention, methods and constructs are provided for reducing MPO activity, reducing alkaloid levels, and producing reduced alkaloid plants. While any method may be used for reducing alkaloid levels, the present invention contemplates antisense, sense co-suppression, RNAi, artificial microRNA, virus-induced gene silencing (VIGS), antisense, sense co-suppression, and targeted mutagenesis approaches.

RNAi techniques involve stable transformation using RNAi plasmid constructs (Helliwell and Waterhouse, *Methods Enzymol.* 392:24-35 (2005)). Such plasmids are composed of a fragment of the target gene to be silenced in an inverted repeat structure. The inverted repeats are separated by a spacer, often an intron. The RNAi construct driven by a suitable promoter, for example, the Cauliflower mosaic virus (CaMV) 35S promoter, is integrated into the plant genome and subsequent transcription of the transgene leads to an RNA molecule that folds back on itself to form a double-stranded hairpin RNA. This double-stranded RNA structure is recognized by the plant and cut into small RNAs (about 21 nucleotides long) called small interfering RNAs (siRNAs). siRNAs associate with a protein complex (RISC) which goes on to direct degradation of the mRNA for the target gene.

Artificial microRNA (amiRNA) techniques exploit the microRNA (miRNA) pathway that functions to silence endogenous genes in plants and other eukaryotes (Schwab et al., *Plant Cell* 18:1121-33 (2006); Alvarez et al, *Plant Cell* 18:1134-51 (2006)). In this method, 21 nucleotide long fragments of the gene to be silenced are introduced into a pre-miRNA gene to form a pre-amiRNA construct. The pre-miRNA construct is transferred into the plant genome using transformation methods apparent to one skilled in the art. After transcription of the pre-amiRNA, processing yields amiRNAs that target genes, which share nucleotide identity with the 21 nucleotide amiRNA sequence.

In RNAi silencing techniques, two factors can influence the choice of length of the fragment. The shorter the fragment the less frequently effective silencing will be achieved, but very long hairpins increase the chance of recombination in bacterial host strains. The effectiveness of silencing also appears to be gene dependent and could reflect accessibility of target mRNA or the relative abundances of the target mRNA and the hpRNA in cells in which the gene is active. A fragment length of between 100 and 800 bp, preferably between 300 and 600 bp, is generally suitable to maximize the efficiency of silencing obtained. The other consideration is the part of the gene to be targeted. 5' UTR, coding region, and 3' UTR fragments can be used with equally good results. As the mechanism of silencing depends on sequence homology there is potential for cross-silencing of related mRNA sequences. Where this is not desirable a region with low sequence similarity to other sequences, such as a 5' or 3' UTR, should be chosen. The rule for avoiding cross-homology silencing appears to be to use sequences that do not have blocks of sequence identity of over 20 bases between the construct and the non-target gene sequences. Many of these same principles apply to selection of target regions for designing amiRNAs.

Virus-induced gene silencing (VIGS) techniques are a variation of RNAi techniques that exploits the endogenous antiviral defenses of plants. Infection of plants with recombinant VIGS viruses containing fragments of host DNA leads to post-transcriptional gene silencing for the target gene. In one embodiment, a tobacco rattle virus (TRV) based VIGS system can be used. Tobacco rattle virus based VIGS systems are described for example, in Baulcombe D. C., Curr. Opin. Plant Biol. 2: 109-113 (1999); Lu R, et al., Methods 30: 296-303 (2003); Ratcliff F. et al., The Plant Journal 25:237-245 (2001); and U.S. Pat. No. 7,229,829

Antisense techniques involve introducing into a plant an antisense oligonucleotide that will bind to the messenger RNA (mRNA) produced by the gene of interest. The "antisense" oligonucleotide has a base sequence complementary to the gene's messenger RNA (mRNA), which is called the "sense" sequence. Activity of the sense segment of the mRNA is blocked by the anti-sense mRNA segment, thereby effectively inactivating gene expression. Application of antisense to gene silencing in plants is described in more detail in Stam et al., *Plant J.* 21:27-42 (2000).

Sense co-suppression techniques involve introducing a highly expressed sense transgene into a plant resulting in reduced expression of both the transgene and the endogenous gene (Depicker and van Montagu, *Curr Opin Cell Biol* 9:373-82 (1997)). The effect depends on sequence identity between transgene and endogenous gene.

Targeted mutagenesis techniques, for example TILLING (Targeting Induced Local Lesions IN Genomes) and "delete-a-gene" using fast-neutron bombardment, may be used to knockout gene function in a plant (Henikoff, et al., *Plant Physiol* 135:630-6 (2004); Li et al. *Plant J.* 27:235-242 (2001)). TILLING involves treating seeds or individual cells with a mutagen to cause point mutations that are then discovered in genes of interest using a sensitive method for single-nucleotide mutation detection. Detection of desired mutations (e.g. mutations resulting in the inactivation of the gene product of interest) may be accomplished, for example, by PCR methods. For example, oligonucleotide primers derived from the gene of interest may be prepared and PCR may be used to amplify regions of the gene of interest from plants in the mutagenized population. Amplified mutant genes may be annealed to wild-type genes to find mismatches between the mutant genes and wild-type genes. Detected differences may be traced back to the plants which had the mutant gene thereby revealing which mutagenized plants will have the desired expression (e.g. silencing of the gene of interest). These plants may then be selectively bred to produce a population having the desired expression. TILLING can provide an allelic series that includes missense and knockout mutations, which exhibit reduced expression of the targeted gene. TILLING is touted as a possible approach to gene knockout that does not involve introduction of transgenes, and therefore may be more acceptable to consumers. Fast-neutron bombardment induces mutations, i.e. deletions, in plant genomes that can also be detected using PCR in a manner similar to TILLING.

Nucleic Acid Constructs

In accordance with one aspect of the invention, a sequence that suppresses alkaloid biosynthesis is incorporated into a nucleic acid construct that is suitable for introducing into a plant or cell. Thus, such a nucleic acid construct can be used to suppress MPO, and optionally at least one of A622, N881, PMT, and QPT in a plant or cell.

In another aspect of the invention, a sequence that increases alkaloid biosynthesis is incorporated into a nucleic acid construct that is suitable for introducing into a plant or cell. Thus, such a nucleic acid construct can be used to overexpress MPO, and optionally at least one of A622, N881, PMT, and QPT in a plant, as well as express MPO and optionally at least one of A622, QPT, PMT, and N881, for example, in a cell.

Recombinant nucleic acid constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence then is cloned into a vector containing suitable regulatory elements, such as upstream promoter and downstream terminator sequences.

An important aspect of the present invention is the use of nucleic acid constructs wherein an alkaloid biosynthesis-encoding sequence is operably linked to one or more regulatory sequences, which drive expression of the alkaloid biosynthesis-encoding sequence in certain cell types, organs, or tissues without unduly affecting normal development or physiology.

"Promoter" connotes a region of DNA upstream from the start of transcription that is involved in recognition and binding of RNA polymerase and other proteins to initiate transcription. A "constitutive promoter" is one that is active throughout the life of the plant and under most environmental conditions. Tissue-specific, tissue-preferred, cell type-specific, and inducible promoters constitute the class of "non-constitutive promoters." "Operably linked" refers to a functional linkage between a promoter and a second sequence, where the promoter sequence initiates and mediates transcription of the DNA sequence corresponding to the second sequence. In general, "operably linked" means that the nucleic acid sequences being linked are contiguous.

Promoters useful for expression of a nucleic acid sequence introduced into a cell to either decrease or increase expression of MPO, A622, N881, PMT, or QPT may be constitutive promoters, such as the carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S" promoter).

Tissue-specific, tissue-preferred, cell type-specific, and inducible promoters may be desirable under certain circumstances. For example, a tissue-specific promoter allows for overexpression in certain tissues without affecting expression in other tissues.

Preferred promoters include promoters which are active in root tissues, such as the tobacco RB7promoter (Hsu et al. *Pestic. Sci.* 44: 9-19 (1995); U.S. Pat. No. 5,459,252), maize promoter CRWAQ81 (US published patent application 20050097633); the *Arabidopsis* ARSK1 promoter (Hwang and Goodman, *Plant J* 8:37-43 (1995)), the maize MR7 promoter (U.S. Pat. No. 5,837,848), the maize ZRP2 promoter (U.S. Pat. No. 5,633,363), the maize MTL promoter (U.S. Pat. Nos. 5,466,785 and 6,018,099) the maize MRS1, MRS2, MRS3, and MRS4 promoters (U.S. Pat. App. 20050010974), an *Arabidopsis* cryptic promoter (U.S. Pat. App. 20030106105) and promoters that are activated under conditions that result in elevated expression of enzymes involved in nicotine biosynthesis such as the tobacco RD2 promoter (U.S. Pat. No. 5,837,876), PMT promoters (Shoji T. et al., *Plant Cell Physiol.* 41: 831-39 (2000b); WO 2002/038588) or an A622 promoter (Shoji T. et al., *Plant Mol Biol.* 50: 427-40 (2002)).

The vectors of the invention may also contain termination sequences, which are positioned downstream of the nucleic acid molecules of the invention, such that transcription of mRNA is terminated, and polyA sequences added. Exemplary of such terminators include *Agrobacterium tumefaciens* nopaline synthase terminator (Tnos), *Agrobacterium tumefaciens* mannopine synthase terminator (Tmas) and the CaMV 35S terminator (T35S). Particularly preferred termination regions for use according to the invention include the pea ribulose bisphosphate carboxylase small subunit termination region (TrbcS) or the Tnos termination region. The expression vector also may contain enhancers, start codons, splicing signal sequences, and targeting sequences.

Expression vectors of the invention may also contain a selection marker by which transformed cells can be identified in culture. The marker may be associated with the heterologous nucleic acid molecule, i.e., the gene operably linked to a promoter. As used herein, the term "marker" refers to a gene encoding a trait or a phenotype that permits the selection of, or the screening for, a plant or cell containing the marker. In plants, for example, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thymidine kinase, xanthine-guanine phospho-ribosyltransferase, glyphosate and glufosinate resistance, and amino-glycoside 3'-O-phosphotransferase (kanamycin, neomycin and G418 resistance). These markers may include resistance to G418, hygromycin, bleomycin, kanamycin, and gentamicin. The construct may also contain the selectable marker gene Bar that confers resistance to herbicidal phosphinothricin analogs like ammonium gluphosinate. Thompson et al., *EMBO J.* 9: 2519-23 (1987). Other suitable selection markers are known as well.

Visible markers such as green florescent protein (GFP) may be used. Methods for identifying or selecting transformed plants based on the control of cell division have also been described. See WO 2000/052168 and WO 2001/059086.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may also be present in the vector, as is known in the art. For instance, when *Agrobacterium* is the host, T-DNA sequences may be included to facilitate the subsequent transfer to and incorporation into plant chromosomes.

Such gene constructs may suitably be screened for activity by transformation into a host plant via *Agrobacterium* and screening for modified alkaloid levels.

Suitably, the nucleotide sequences for the genes may be extracted from the Genbank™ nucleotide database and searched for restriction enzymes that do not cut. These restriction sites may be added to the genes by conventional methods such as incorporating these sites in PCR primers or by sub-cloning.

Preferably, constructs are comprised within a vector, most suitably an expression vector adapted for expression in an appropriate host (plant) cell. It will be appreciated that any vector which is capable of producing a plant comprising the introduced DNA sequence will be sufficient.

Suitable vectors are well known to those skilled in the art and are described in general technical references such as Pouwels et al., Cloning Vectors. A Laboratory Manual, Elsevier, Amsterdam (1986). Particularly suitable vectors include the Ti plasmid vectors.

Genetic Engineering and Selection

The present invention comprehends the genetic manipulation of a plant or cell for regulating alkaloid synthesis via introducing a polynucleotide sequence that encodes an enzyme in the alkaloid synthesis pathway. Accordingly, the present invention provides methodology and constructs for reducing or increasing alkaloid synthesis in a plant. Additionally, the invention provides methods for producing alkaloids and related compounds in a host cell, such as bacteria, yeast, filamentous fungi, algae, green plants, and mammalian cells.

"Genetic engineering" encompasses any methodology for introducing a nucleic acid or specific mutation into a host organism. For example, a plant is genetically engineered when it is transformed with a polynucleotide sequence that suppresses expression of a gene, such that expression of a target gene is reduced compared to a control plant. A plant is genetically engineered when a polynucleotide sequence is introduced that results in the expression of a novel gene in the plant, or an increase in the level of a gene product that is naturally found in the plants. In the present context, "genetically engineered" includes transgenic plants and plant cells, as well as plants and plant cells produced by means of targeted mutagenesis effected, for example, through the use of chimeric RNA/DNA oligonucleotides, as described by Beetham et al., *Proc. Natl. Acad. Sci. USA* 96: 8774-8778 (1999) and Zhu et al., *Proc Natl Acad Sci USA.* 96:8768-8773 (1999), or so-called "recombinagenic olionucleobases," as described in PCT application WO 2003/013226. Likewise, a genetically engineered plant or plant cell may be produced by the introduction of a modified virus, which, in turn, causes a genetic modification in the host, with results similar to those produced in a transgenic plant, as described herein. See, e.g., U.S. Pat. No. 4,407,956. Additionally, a genetically engineered plant or plant cell may be the product of any native approach (i.e., involving no foreign nucleotide sequences), implemented by introducing only nucleic acid sequences derived from the host plant species or from a sexually compatible plant species. See, e.g., U.S. published patent application No. 2004/0107455.

A. Plants

"Plant" is a term that encompasses whole plants, plant organs (e. g. leaves, stems, roots, etc.), seeds, differentiated or undifferentiated plant cells, and progeny of the same. Plant material includes without limitation seeds suspension cultures, embryos, meristematic regions, callus tissues, leaves, roots, shoots, stems, fruit, gametophytes, sporophytes, pollen, and microspores. The class of plants which can be used in the present invention is generally as broad as the class of higher plants amenable to genetic engineering techniques, including both monocotyledonous and dicotyledonous plants, as well as gymnosperms. A preferred nicotine-producing plant includes *Nicotiana, Duboisia, Solanum, Anthocercis*, and *Salpiglessis* genera in the Solanaceae or the *Eclipta* and *Zinnia* genera in the Compositae.

"Tobacco" or "tobacco plant" refers to any species in the *Nicotiana* genus that produces nicotinic alkaloids, including but are not limited to the following: *Nicotiana acaulis, Nicotiana acuminata, Nicotiana acuminata* var. *multzjlora, Nicotiana africana, Nicotiana alata, Nicotiana amplexicaulis, Nicotiana arentsii, Nicotiana attenuata, Nicotiana benavidesii, Nicotiana benthamiana, Nicotiana bigelovii, Nicotiana bonariensis, Nicotiana cavicola, Nicotiana clevelandii, Nicotiana cordifolia, Nicotiana corymbosa, Nicotiana debneyi, Nicotiana excelsior, Nicotiana forgetiana, Nicotiana fragrans, Nicotiana glauca, Nicotiana glutinosa, Nicotiana goodspeedii, Nicotiana gossei, Nicotiana hybrid, Nicotiana ingulba, Nicotiana kawakamii, Nicotiana knightiana, Nicotiana langsdorfi, Nicotiana linearis, Nicotiana longiflora, Nicotiana maritima, Nicotiana megalosiphon, Nicotiana miersii, Nicotiana noctiflora, Nicotiana nudicaulis, Nicotiana obtusifolia, Nicotiana occidentalis, Nicotiana occidentalis* subsp. *hesperis, Nicotiana otophora, Nicotiana paniculata, Nicotiana pauczjlora, Nicotiana petunioides, Nicotiana plumbaginifolia, Nicotiana quadrivalvis, Nicotiana raimondii, Nicotiana repanda, Nicotiana rosulata, Nicotiana rosulata* subsp. *ingulba, Nicotiana rotundifolia, Nicotiana rustica, Nicotiana setchellii, Nicotiana simulans, Nicotiana solanifolia, Nicotiana spegauinii, Nicotiana stocktonii, Nicotiana suaveolens, Nicotiana sylvestris, Nicotiana tabacum, Nicotiana thyrsiflora, Nicotiana tomentosa, Nicotiana tomentosifomis, Nicotiana trigonophylla, Nicotiana umbratica, Nicotiana undulata, Nicotiana velutina, Nicotiana wigandioides*, and *Nicotiana x sanderae*.

"Tobacco product(s)" refers to a product comprising material produced by a *Nicotiana* plant, including for example, nicotine gum and patches for smoking cessation, cigarette tobacco including expanded (puffed) and reconstituted tobacco, cigar tobacco, pipe tobacco, cigarettes, cigars, and all forms of smokeless tobacco such as chewing tobacco, snuff, snus and lozenges.

The Erythroxylaceae (or coca family) is a family of flowering plants consisting of 4 genera and about 240 species. The best-known species by far is the coca (*Erythroxylum coca*). It has been previously reported that when labeled 4-methylaminobutanal diethyl acetal (an acetal derivative of N-methylpyrrolinium cation) was fed to the leaf of *Erythroxylum coca*, the label was incorporated into the tropane moiety of cocaine. Leete, Planta Med. 56: 339-352 (1990). Therefore, it is reasonable to expect that the MPO genes of the present invention are involved in the formation of cocaine.

As known in the art, there are a number of ways by which genes and gene constructs can be introduced into plants, and a combination of plant transformation and tissue culture techniques have been successfully integrated into effective strategies for creating transgenic crop plants.

These methods, which can be used in the present invention, have been described elsewhere (Potrykus, *Annu. Rev. Plant Physiol. Plant Mol. Biol.* 42:205-225 (1991); Vasil, *Plant Mol. Biol.* 5:925-937 (1994); Walden and Wingender, *Trends Biotechnol.* 13:324-331 (1995); Songstad et al., *Plant Cell, Tissue and Organ Culture* 40:1-15 (1995)), and are well known to persons skilled in the art. For example, one skilled in the art will certainly be aware that, in addition to *Agrobacterium*-mediated transformation of *Arabidopsis* by vacuum infiltration (Bechtold et al., C. R. Acad. Sci. Ser. III Sci. Vie, 316:1194-1199 (1993)) or wound inoculation (Katavic et al., Mol. Gen. Genet. 245:363-370 (1994)), it is equally possible to transform other plant and crop species, using *Agrobacterium* Ti-plasmid-mediated transformation (e.g., hypocotyl (DeBlock et al., *Plant Physiol.* 91:694-701 (1989)) or cotyledonary petiole (Moloney et al., *Plant Cell Rep.* 8:238-242 (1989) wound infection), particle bombardment/biolistic methods (Sanford et al., *J. Part. Sci. Technol.* 5:27-37 (1987); Nehra. et al., *Plant J.* 5:285-297 (1994); Becker et al., *Plant J.* 5:299-307 (1994)) or polyethylene glycol-assisted protoplast transformation (Rhodes et al., Science 240:204-207 (1988); Shimamoto et al., Nature 335: 274-276 (1989)) methods.

*Agrobacterium rhizogenes* may be used to produce transgenic hairy roots cultures of plants, including tobacco, as described, for example, by Guillon et al., *Curr. Opin. Plant Biol.* 9:341-6 (2006). "Tobacco hairy roots" refers to tobacco roots that have T-DNA from an Ri plasmid of *Agrobacterium rhizogenes* integrated in the genome and grow in culture without supplementation of auxin and other phytohormones. Tobacco hairy roots produce nicotinic alkaloids as roots of a whole tobacco plant do.

Additionally, plants may be transformed by *Rhizobium, Sinorhizobium* or *Mesorhizobium* transformation. (Broothaerts et al., Nature 433:629-633 (2005)).

After transformation of the plant cells or plant, those plant cells or plants into which the desired DNA has been incorporated may be selected by such methods as antibiotic resistance, herbicide resistance, tolerance to amino-acid analogues or using phenotypic markers.

Various assays may be used to determine whether the plant cell shows a change in gene expression, for example, Northern blotting or quantitative reverse transcriptase PCR (RT-PCR). Whole transgenic plants may be regenerated from the transformed cell by conventional methods. Such transgenic plants may be propagated and self-pollinated to produce homozygous lines. Such plants produce seeds containing the genes for the introduced trait and can be grown to produce plants that will produce the selected phenotype.

Modified alkaloid content, effected in accordance with the present invention, can be combined with other traits of interest, such as disease resistance, pest resistance, high yield or other traits. For example, a stable genetically engineered transformant that contains a suitable transgene that modifies alkaloid content may be employed to introgress a modified alkaloid content trait into a desirable commercially acceptable genetic background, thereby obtaining a cultivar or variety that combines a modified alkaloid level with said desirable background. For example, a genetically engineered tobacco plant with reduced nicotine may be employed to introgress the reduced nicotine trait into a tobacco cultivar with disease resistance trait, such as resistance to TMV, blank shank, or blue mold. Alternatively, cells of a modified alkaloid content plant of the present invention may be transformed with nucleic acid constructs conferring other traits of interest.

B. Cells

The invention contemplates genetically engineering a cell with a nucleic acid sequence encoding an enzyme involved in the production of alkaloids. Illustrative cells include but are not limited to plant cells, such as *Atropa belladonna, Hyoscyamus niger, Arabidopsis thaliana*, as well as insect, mammalian, yeast, fungal, algal, or bacterial cells. Suitable host cells are discussed further in Goeddel, GENE EXPRESSION TECHNOLOGY: METHODS IN ENZYMOLOGY 185, Academic Press, San Diego, Calif. (1990).

"Insect cell" refers to any insect cell that can be transformed with a gene encoding an alkaloid biosynthesis enzyme and is capable of expressing in recoverable amounts the enzyme or its products. Illustrative insect cells include Sf9 cells (ATCC CRL 1711).

"Fungal cell" refers to any fungal cell that can be transformed with a gene encoding an alkaloid biosynthesis enzyme and is capable of expressing in recoverable amounts the enzyme or its products. Illustrative fungal cells include yeast cells such as *Saccharomyces cerevisiae* (Baldari, et al., 1987. *EMBO J.* 6: 229-234) and *Pichia pastoris* (e.g. *P. pastoris* KM714 available from Invitrogen). Cells of filamentous fungi such as *Aspergillus* and *Trichoderma* may also be used. Archer, et al., *Antonie van Leeuwenhoek* 65: 245-250 (2004).

"Bacterial cell" refers to any bacterial cell that can be transformed with a gene encoding an alkaloid biosynthesis enzyme and is capable of expressing in recoverable amounts the enzyme or its products. Illustrative bacterial cells include *E. coli*, such as *E. coli* strain M15/rep4, which is available commercially from QIAGEN.

"Mammalian cell" refers to any mammalian cell that can be transformed with a gene encoding an alkaloid biosynthesis enzyme and is capable of expressing in recoverable amounts the enzyme or its products. Illustrative mammalian cells include Chinese hamster ovary cells (CHO) or COS cells. Mammalian cells may also include a fertilized oocyte or an embryonic stem cell into which nicotinic alkaloid biosynthesis enzyme-coding sequences have been introduced. Such host cells can then be used to create non-human transgenic animals. Examples of systems for regulated expression of proteins in mammalian cells include Clontech's Tet-Off and Tet-On gene expression systems and similar systems. Gossen and Bujard, *Proc. Natl. Acad. Sci. USA* 89: 55475551 (1992).

"Algae cell" refers to any algae species that can be transformed with a gene encoding an alkaloid biosynthesis enzyme without adversely affecting normal algae development or physiology. Illustrative algae cells include *Chlamydomonas reinhardtii* (Mayfield and Franklin, *Vaccine* 23: 1828-1832 (2005).

Since production of alkaloids in an insect cell could adversely affect insect growth and development, an inducible expression system may mitigate adverse affects. For example, insect cells may be first grown under non-inducing conditions to a desired state and then expression of the enzyme is induced.

Additionally, cells expressing alkaloid biosynthesis genes may be supplied with precursors to increase substrate availability for nicotinic alkaloid synthesis. Cells may be supplied with analogs of precursors which may be incorporated into analogs of naturally occurring nicotinic alkaloids.

Constructs according to the invention may be introduced into any cell, using a suitable technique, such as *Agrobacterium*-mediated transformation for plant cells, particle bombardment, electroporation, and polyethylene glycol fusion, calcium phosphate transfection, DEAE-dextran mediated transfection, or cationic lipid-mediated transfection.

Such cells may be genetically engineered with a nucleic acid construct of the present invention without the use of a selectable or visible marker and transgenic organisms may be identified by detecting the presence of the introduced construct. The presence of a protein, polypeptide, or nucleic acid molecule in a particular cell can be measured to determine if, for example, a cell has been successfully transformed or transfected. For example, and as routine in the art, the presence of the introduced construct can be detected by PCR or other suitable methods for detecting a specific nucleic acid or polypeptide sequence. Additionally, genetically engineered cells may be identified by recognizing differences in the growth rate or a morphological feature of a transformed cell compared to the growth rate or a morphological feature of a non-transformed cell that is cultured under similar conditions. See WO 2004/076625.

IV. Quantifying Alkaloid Content

A. Reduced Alkaloids

Pursuant to one aspect of the invention, genetically engineered plants and cells are characterized by reduced alkaloid content.

A quantitative reduction in alkaloid levels can be assayed by several methods, as for example by quantification based on gas-liquid chromatography, high performance liquid chromatography, radio-immunoassays, and enzyme-linked immunosorbent assays. In the present invention, alkaloid levels were measured by HPLC analysis performed on a Waters 2695 separations module equipped with a Waters X-Terra RP18 5 μm 4.6×150 mm with precolumn at a column temperature of 60°. The isocratic elution system consisted of 80% A: 20% B where solvent A consisted of 50 mM citrate, 10 mM octanesulfonic acid pH 3.0 (adjusted with triethylamine) containing 5% MeOH and solvent B was methanol over 15 min at a flow rate of 1 ml/min. Injection volume was 20 μl. Nicotine was detected at 261 nm via photodiode array detection.

In describing a plant of the invention, the phrase "decreased alkaloid plant" or "reduced alkaloid plant" encompasses a plant that has a decrease in alkaloid content to a level less than 50%, and preferably less than 10%, or 1% of the alkaloid content of a control plant of the same species or variety.

B. Increased Alkaloids

In one aspect of the invention, genetically engineered plants and cells are characterized by increased alkaloid content. Similarly, genetically engineered cells are characterized by increased alkaloid production.

In describing a plant of the invention, the phrase "increased alkaloid plant" encompasses a genetically engineered plant that has an increase in alkaloid content greater than 10%, and preferably greater than 50%, 100%, or 200% of the alkaloid content of a control plant of the same species or variety.

A successfully genetically engineered cell is characterized by nicotinic alkaloid synthesis. For example, an inventive genetically engineered cell may produce more nicotine compared to a control cell.

A quantitative increase in nicotinic alkaloid levels can be assayed by several methods, as for example by quantification based on gas-liquid chromatography, high performance liquid chromatography, radio-immunoassays, and enzyme-linked immunosorbent assays. In the present invention, alkaloid levels were measured by high performance liquid chromatography with a reversed phase column and a photodiode array detector as described above.

Products

The MPO gene may be used for production of MPO in host cells. Additionally, products can be made using the activity of recombinant MPO. For example, recombinant MPO may be used for the synthesis, or partial synthesis, of alkaloids. MPO will act on some analogs of N-methyl putrescine to produce products that do not occur naturally. See Boswell et al., *Phytochemistry* 52:855-869 (1999); Boswell et al., *Phytochemistry* 52:871-878 (1999). Thus, recombinant MPO should be useful in the production of alkaloid analogs including nicotine analogs. To this end, large-scale or commercial quantities of MPO can be produced by a variety of methods, including extracting recombinant enzyme from a genetically engineered plant, cell, or culture system, including but not limited to hairy root cultures, insect, bacterial, fungal, plant, algae, mammalian cell culture and in vitro translation systems.

In the following examples, functional genomics was used to elucidate an MPO gene that plays an important role in pyrrolidine alkaloid (e.g. nicotine) and tropane alkaloid (e.g. scopolamine and cocaine) biosynthesis. ESTs were obtained from the model plant *Nicotiana benthamiana* by sequencing subtractive cDNA libraries enriched for genes expressed in methyljasmonate-treated *N. benthamiana* roots. The EST dataset was analyzed for the presence of DNA sequences that may encode enzymes of the nicotine biosynthetic pathway. Candidate genes were silenced using virus-induced gene silencing (VIGS), with silencing genes involved in nicotine biosynthesis leading to significant reductions in nicotine levels.

The data from the present experiments indicate that the gene isolated from *Nicotiana benthamiana* encodes N-methylputrescine oxidase (MPO), which functions in nicotine biosynthesis. These results show that the cloned MPO belongs to the amine oxidase superfamily which occurs widely in prokaryotes and eukaryotes and contains a tightly bound Cu II and 6-hydroxydopa quinone (TPQ) moiety derived from tyrosine.

These examples are meant to be illustrative only and are not to be read as limiting the present invention.

Example 1. Construction of Subtractive cDNA Libraries, EST Sequencing and Selection of MPO Candidate Genes Nicotine biosynthesis occurs in the roots of *Nicotiana* species (Dawson R F, Science 94: 396-397 (1941)) and is induced by insect damage, wounding and the application of jasmonates (Winz R A et al., *Plant Physiol.* 125: 2189-2202 (2001)). In order to identify genes encoding enzyme nicotine biosynthesis enzymes, a novel approach was used that combined expressed sequence tag (EST) sequencing of methyljasmonate (MeJa)-induced roots of *Nicotiana benthamiana* with functional analysis using virus-induced gene silencing (VIGS).

Hydroponic Cultivation of *Nicotiana benthamiana*

*Nicotiana benthamiana* (Solanaceae) seedlings were grown hydroponically in 0.25× Hoagland's solution supplemented with iron chelate solution and oxygenated using an aquarium bubbler. Roots from three-week old plants were sampled before (t=0) and at 1, 4, and 7 hours after addition of MeJa to a final concentration of 11 µM. Total RNA was isolated from 450 mg each of untreated leaves, untreated roots, and a combined MeJa-treated root sample composed of 150 mg roots each from the 1, 4 and 7 hour time points using a RNeasy midi kit (Qiagen). We constructed three separate subtractive cDNA libraries: NBREL2, with mRNA pooled from MeJa-treated roots as tester and untreated root mRNA as driver; NBLEL3, with mRNA pooled from MeJa-treated roots as tester and leaf mRNA as driver; and NBREL4, with mRNA pooled from MeJa-treated roots as both tester and driver.

Construction of Subtracted VIGS-cDNA Library

A PCR-select subtractive cDNA library kit (Clontech) was used for cDNA synthesis with some modifications. Briefly, about 250 µg of total RNA was mixed with 300 µl of Oligo $(dT)_{25}$ Dynabeads (Dynal Biotech) in binding buffer (20 mM Tris-HCl pH 7.5, 1 M LiCl, 2 mM EDTA). After 10 min incubation, the beads was washed three times with washing buffer B (10 mM Tris-HCl pH 7.5, 0.15M LiCl, 1 mM EDTA), followed by washing twice with first strand buffer. The washed beads containing mRNA was resuspended in 40 µl of cDNA synthesis cocktail (8 µl 5× first strand buffer, 4 µl 10 mM dNTPs, 24 µl RNase-free water and 4 µl (8U) AMV reverse transcriptase) and incubated at 42° C. for 1.5 hours. The second strand synthesis was completed by addition of 120 µl of second strand synthesis cocktail (32 µl of 5× second strand buffer, 3.2 µl of 10 mM dNTPs, 8 µl of 20× enzyme cocktail and 77 µl RNase free water) and incubation at 16° C. for 2 hours, followed by addition of 4 µl (12U) T4 DNA polymerase and further incubation for 30 min. The reaction was stopped by addition of 20 µl 0.5 M EDTA. The beads were magnetically separated, the supernatant removed and the beads resuspended in 500 µl of wash buffer (5 mM Tris-HCl pH 7.5, 0.5 mM EDTA, 1 M NaCl, 1% SDS and 10 µg/ml glycogen) and heated at 75° C. for 15 min. The beads were then washed three times with wash buffer (5 mM Tris-HCl pH7.5, 0.5 mM EDTA, 1 M NaCl and 200 µg/ml BSA), followed by two more washes with Rsal buffer. The beads were resuspended in 84 µl $H_2O$, 10 µl 10× Rsal buffer, 3 µl (30 U) Rsal, and incubated at 37° C. overnight. The free cDNA was isolated by magnetic separation of the beads and was used for adapter ligation, hybridizations and primary PCR as described in the manufacturer's protocol. Secondary PCR was performed using primers 5'-CGG-GATCCTCGAGCGGCCGCCCGGGCAGGT-3' (BamHI site underlined) and 5'-CGGAAT-TCAGCGTGGTCGCGGCCGAGGT-3' (EcoR1 site underlined). The PCR-select amplified cDNA fragments (700 ng) were digested with EcoRI and BamHI, followed by ligation into a similarly digested TRV-RNA2 vector, pYL156 (Liu Y, et al., Plant J. 30: 415-429, 2002). The ligation mixture was electroporated into DH10B *E. coli* competent cells to give primary libraries. These was amplified on agar plates, plasmid DNA isolated and used to transform *Agrobacterium tumefaciens* C58 via electroporation. The ligation efficiency as determined by colony PCR was 98%.

EST Sequencing of Subtracted VIGS-cDNA Library and Identification of MPO Candidates To amplify cDNA inserts for sequencing, PCR was performed using vector primers 5'-GTTACT-CAAGGAAGCACGATGAG-3' and 5'-CAGTCGAGAATGTCAATCTCGTAG-3' and randomly selected *A. tumefaciens* colonies as template. The resulting PCR products were sequenced directly using BigDye terminators and the primer 5'-GTTACTCAAGGAAGCAC-GATGAG-3'. 2016 ESTs were sequenced from NBREL2, and 1920 each from NBLEL3 and NBREL4. After removal of poor quality sequences, and combining of the three datasets, we obtained 3480 unique transcripts consisting of 606 contigs and 2874 singletons. The total VIGS-EST dataset was annotated via BLASTX comparison to the NCBI non-redundant database.

It has been shown that N-methylputrescine oxidase (MPO), a key enzyme in the biosynthesis of nicotine and other alkaloids (FIG. 1), is a copper-containing quinoprotein that oxidases N-methylputrescine to form N-methylaminobutanal (Mizusaki S. et al., *Phytochemistry* 11: 2757-2762, (1972); Davies H M et al., *Phytochemistry* 28: 1573-1578 (1989)). N-methylaminobutanal spontaneously cyclizes to yield N-methylpyrrolinium ion. Using a keyword search of BLASTX results, we identified seven ESTs that were annotated as copper amine oxidases. The seven clones formed two clusters (CL181contig1, 3 members; CL547contig1, 2 members) and three singletons (Table 1).

Example 2. Cloning of Full-Length cDNA for N-Methylputrescine Oxidase Candidate Gene cDNA fragments were used for EST sequencing and VIGS analyses and therefore it was necessary to obtain the full-length cDNA sequence using RACE PCR.
RACE PCR of Full-Length cDNA for N-Methylputrescine Oxidase Candidate Gene To obtain the 5' cDNA end of MPO, 5 µg of total RNA from MeJa-treated *N. benthamiana* roots was reverse transcribed using a GeneRacer kit (Invitrogen) according to manufacturer's protocol. 5' RACE PCR reactions were performed with a GeneRacer 5' primer and a gene specific primer (5'-CTTGAGCATCTATGGGTGGC-3') using PCR program (95° C. 2 min; 35 cycles 95° C. 30 sec, 58° C. 30 sec, 66° C. 30 sec, 72° C. 1 min; 72° C. 10 min) and Pfu Turbo polymerase (Stratagene). The 3' RACE reaction were performed with a GeneRacer 3' primer and gene specific primer (5'-AGCAATGCGTGACTGTGATCCG-3') using the same PCR program. The resulting blunt-end PCR products were cloned into the pCR4Blunt-TOPO vector (Invitrogen) and sequenced from both ends.

The full-length MPO gene was 2738 bp in length encoding an open reading frame (ORF) of 2379 bp. The sequence of this MPO gene is set forth in SEQ ID NO: 1. The sequence of the MPO open reading frame (ORF) is set forth in SEQ ID NO: 2. The predicted amino acid sequence is set forth in SEQ ID NO: 3.

Based on computer analysis of primary amino acid sequence (SEQ ID No: 3), the *Nicotiana* MPO contains several domains that are characteristic of copper-containing amine oxidases. Amino acid residues 96-141 form copper amine oxidase domain N2, and amino acid residues 221-325 form copper amine oxidase domain N3. A conserved tyrosine at MPO amino acid position 514 is post-translationally-modified into the redox factor topaquinone (TPQ). Conserved histidine residues at positions 562, 564 and 728 may function in copper-binding. As such, it is apparent that an MPO from a corresponding species would likely be more highly conserved throughout these regions and would contain similar domains. A high degree of identity across species in these domains provides target regions in the *Nicotiana* MPO gene for nucleotide sequences useful in the preparation of interfering RNA or other gene silencing constructs that function in other related species of plants.

Example 3. Analysis of Expression of MPO Candidate Genes

Nicotine biosynthesis occurs in the roots of *Nicotiana* species, as evidenced by the root-specific expression of putrescine N-methyltransferase (PMT) and other enzymes catalyzing reactions in the nicotine pathway (Sinclair S J et al., *Functional Plant Biol.* 31: 721-729, (2004)). In order to determine if the cloned MPO was expressed in roots, and was inducible by MeJa, we used reverse transcription-PCR (RT-PCR) to measure the levels of MPO transcript.
RT-PCR Analysis of MPO and PMT Expression in Different *N. benthamiana* Tissues Reverse transcription-PCR (RT-PCR) was used to determine the expression of MPO in different *N. benthamiana* tissues in comparison to PMT, a known enzyme of the nicotine biosynthetic pathway and a step postulated to be immediately upstream of MPO (FIG. 1). RNA was isolated from *N. benthamiana* tissues (young leaf, old leaf, stem, main root, lateral (side) root and whole seedlings) using an RNeasy Plant Mini kit (Qiagen) using the manufacturer's protocol. First strand cDNA was synthesized from 1.7 µg total RNA as described procedure in SuperScript III first-strand synthesis system for RT-PCR (Invitrogen), followed by PCR amplification of 2 µl cDNA in 50 µl reaction volume using PCR program (95° C. 30 sec, 58° C. 30 sec, 72° C. 50 sec for 30 cycles) and Taq polymerase. Primers for actin were 5'-CTACAATGAGCTTCGTGTTGC-3' and 5'-TGCT-GAGGGAAGCCAAGATA-3', for PMT 5'-TCATGCTCTTTGAGTCAGCAA'-3' and 5'-CACCAGTGTTCATTGTTCACT-3' and for MPO 5'-AGGTGGACATCACAGAGGAA-3' and 5'-AGTCGTTTCAACTCCTCCCGTA-3'. Aliquots of each reaction were analyzed on a 1% agarose gel containing ethidium bromide.

Figure 2:
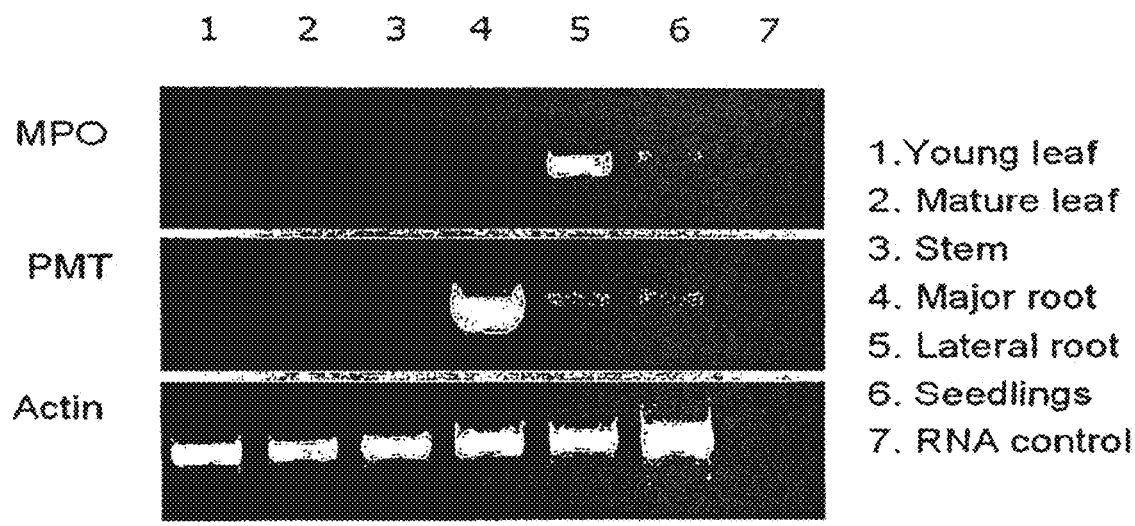
FIG. 2 depicts RT-PCR analysis of MPO expression in different tissues of *Nicotiana benthamiana*.

As shown in FIG. 2, MPO showed its greatest expression in the fine, lateral roots of *N. benthamiana* plants. MPO transcript was also detected in major root tissue and in whole seedlings, which include root and leaf tissue. The root-specific expression of MPO therefore supported its role in nicotine biosynthesis.
qRT-PCR Analysis of MPO and PMT Expression in MeJa-Treated *N. benthamiana* Roots The inducibility of MPO by MeJa application was determined using quantitative RT-PCR (qRT-PCR). The same PCR primers were used as for RT-PCR analysis of expression in different tissues. Total RNA was extracted from hydroponically grown roots immediately before and 1, 4, and 7 hours after addition of MeJa (11 µM) to the hydroponic solution. Hydroponic conditions are detailed in Example 1. RNA was isolated using a Plant RNeasy kit (Qiagen). qRT-PCR was carried out as described in SuperScript III platinum SYBR green two-step qRT-PCR kit (Invitrogen) using an iCycler iQ Real-Time detection system (BioRad). Briefly, 1.7 µg total RNA was used in the first strand cDNA synthesis in 20 µl reaction volume, followed by real-time PCR amplification of 1 µl cDNA in 25 µl reaction volume under 95° C. 30 sec, 58° C. 15 sec, 72° C. 50 sec for 40 cycles in 96-well optical PCR plate (BioRad). The change of target gene expression level was obtained using the method of Ramakers et al. (*Neuroscience Letters* 339: 62-66 (2003)) with actin as a reference gene for transcript normalization.

Figure 3:
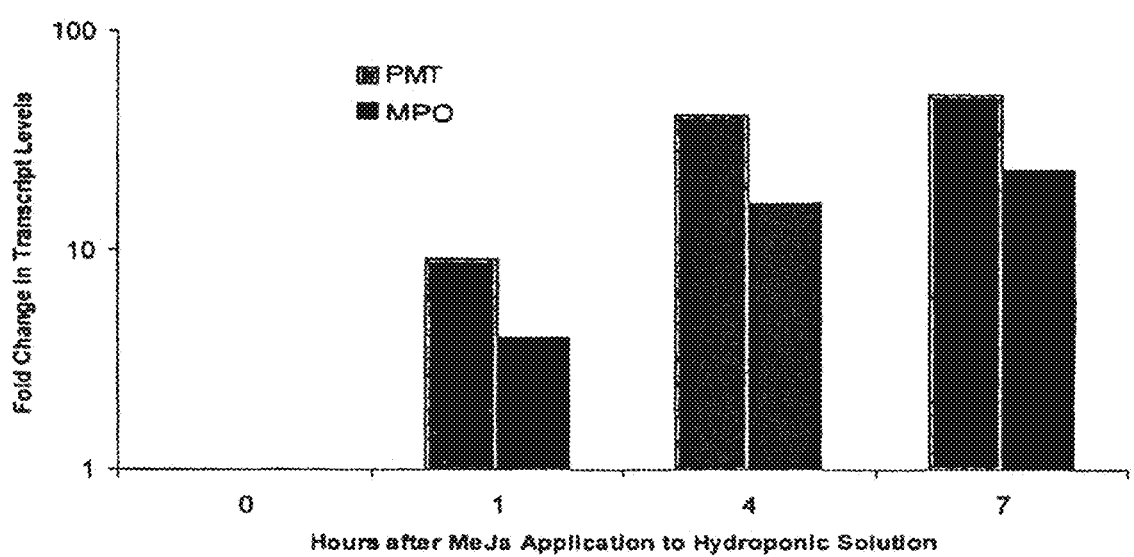
FIG. 3 depicts quantitative RT-PCR (qRT-PCR) analysis of PMT and MPO expression in roots of *N. benthamiana* in response to treatment with methyljasmonate (MeJa).

The change in expression of PMT and MPO in response to MeJa application is shown in FIG. 3. MeJa application increased MPO expression 23-fold over pre-induction levels. MPO expression paralleled that of PMT, although the latter showed an even more dramatic increase in transcript levels in response to the inducer.

Example 4. Silencing MPO Expression in Plants Using Virus-Induced Gene Silencing (VIGS)

Virus-induced gene silencing (VIGS) was used to test the effect of silencing the candidate MPO gene on nicotine biosynthesis. VIGS is a functional genomics tool that allows for rapid loss- or reduction-of-function experiments in plants (Baulcombe D. C., *Curr. Opin. Plant Biol.* 2: 109-113 (1999)). The advantages and disadvantages of VIGS have been reviewed (Lu R, et al., *Methods* 30: 296-303 (2003)).

VIGS Silencing Constructs Containing MPO Fragments

Three independent VIGS constructs representing different regions of MPO were tested for their ability to reduce nicotine levels. The positions of these fragments relative to the MPO ORF are shown in FIG. 4. VIGS construct 214D11 was 378 bp in length and corresponded to nucleotide positions 754-1132 of the full-length MPO cDNA. 214D11 was in the reverse (antisense orientation) relative to the tobacco rattle virus (TRV) coat protein. IGS construct 317A08 was 252 bp in length and corresponded to nucleotide positions 1521-1772 of the full-length MPO cDNA. 317A08 was also in the reverse orientation. VIGS construct 403601 was 277 bp in length and corresponded to nucleotide positions 1129-1405 of the full-length MPO cDNA. 403601 was in the forward (sense) orientation relative to the TRV coat protein.

VIGS Methods

*N. benthamiana* plants were grown in soil in a controlled environment chamber with 16 hour/23° days and 8 hour/20° nights under approximately 100 µmol/m$^2$/s light intensity. Cultures of *A. tumefaciens* C58 containing the TRV-RNA1 plasmid or TRV-RNA2 constructs (pYL156) (Liu et al, 2002) were grown overnight at 28° C. After centrifugation, the bacterial cell pellet was resuspended in infiltration buffer containing 1 mM MES (pH 5), 10 mM MgCl$_2$ and 100 µM acetosyringone to $OD_{600}$=1 and allowed to stand at room temperature for 3-6 hours before infiltration. Suspensions of TRV-RNA1 and TRV-RNA2 constructs were mixed 1:1 and infiltrated into the underside of the upper leaves of 3-4 week old plants using a 1 ml syringe. Negative control plants were infiltrated with buffer only or a TRV-RNA2 construct containing a non-functional fragment of green fluorescent protein (GFP). Plants were grown for 3 weeks before leaf nicotine levels were measured using ion-pair HPLC.

Nicotine Analysis by Ion-Pair HPLC

Samples of young (~3-5 cm) leaves were utilized by excising one half of a leaf from each plant. After determining the fresh weight of the sample, 200 µl of zirconium beads and 300 µl of 50 mM citrate buffer pH 3: methanol (70:30) were added, the sample was homogenized with a Beadbeater followed by incubation in an ultrasonic bath for 10 min. The resulting extract was incubated at 4° overnight before centrifugation and filtration (0.45 µm, Spin-X) to clarify the extract. Ion-pair HPLC analysis was performed on a Waters 2695 separations module equipped with a Waters X-Terra RP18 5 µm 4.6×150 mm with precolumn at a column temperature of 60°. The isocratic elution system consisted of 80% A: 20% B where solvent A consisted of 50 mM citrate, 10 mM octanesulfonic acid pH 3.0 (adjusted with triethylamine) containing 5% MeOH and solvent B was methanol over 15 min at a flow rate of 1 ml/min. Injection volume was 20 µl. Nicotine was detected at 261 nm via photodiode array detection. Quantification was performed using peak area by comparison to a standard curve ($r^2$ 0.999) derived from injection of solutions of authentic nicotine ranging in concentration from 1040 µg/ml to 10.4 µg/ml.

Figure 5A:
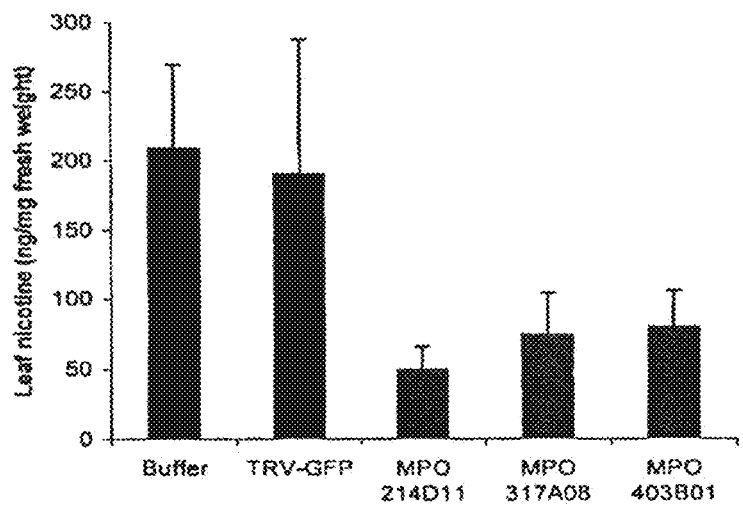
FIG. 5A depicts nicotine content of leaves sampled from control plants and plants treated with MPO VIGS vectors as determined by HPLC analysis.
Figure 5B:
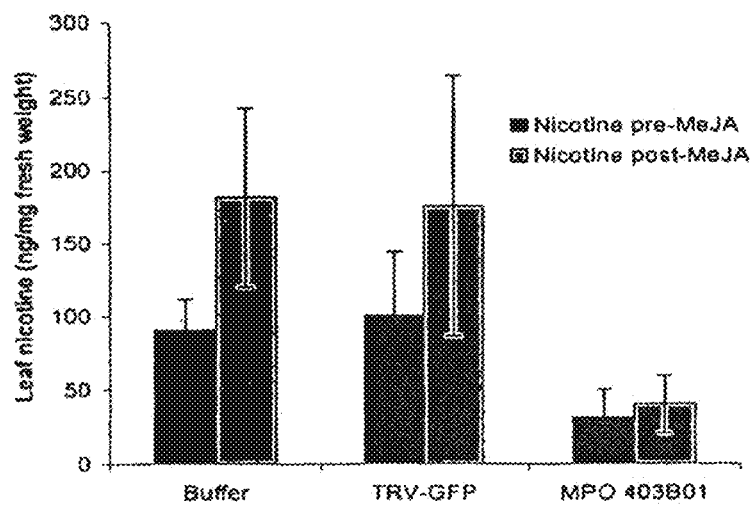
FIG. 5B depicts changes in nicotine levels in control plants and plants infected with TRV-MPO construct 403B01 in response to methyljasmonate (MeJa) application.

All three MPO VIGS constructs reduced constitutive nicotine levels in infected plants (FIG. 5). TRV-GFP control plants had similar nicotine levels to buffer only treated plants, indicating that TRV infection had little influence on nicotine biosynthesis. We chose the VIGS construct 403601 for retesting. Nicotine levels in plants infected with 403601 were determined before and five-days after spraying the leaves with MeJa (0.1% (v/v) in water containing 0.1% (v/v) Tween-20) (FIG. 4). Using construct 403601, MeJa-induced nicotine levels were reduced by 77% in MPO silenced plants compared with TRV-GFP controls.

Measurement of N-Methylputrescine Levels in MPO Silenced Plants

Polyamines in the roots of MPO-silenced plants were measured using a method of Minocha S C et al., (*J. Chromatography* 511: 177-183 (1990)). Briefly, root tissue was frozen in liquid nitrogen and ground to a fine powder. After determining fresh weight of the sample, 200 µl of zirconium beads and 300 µl of ice cold 5% perchloric acid containing 100 nmol/ml of 1,7 diaminoheptane (DAH) were added and the sample homogenized with a Beadbeater. The extract was clarified by centrifugation and filtration (0.45 µm, Spin-X). One hundred µl of saturated sodium carbonate was added to a 50 µl aliquot of each sample, followed by the addition of 100 µl dansyl chloride (10 mg/ml). The samples were mixed by vortexing and then incubated at 60° for 1 hour in the dark. Fifty µl of proline (100 mg/ml in 5% perchloric acid) was added to react with the remaining dansyl chloride. The reaction was extracted with 400 µl toluene, vortexed and the organic phase separated by centrifugation. A 200-µl aliquot of the toluene layer was dried by SpeedVac and the residue resuspended in 1 ml of acetonitrile. Ion-pair HPLC analysis was performed on a Waters 2695 separations module equipped with a Waters X-Terra RP18 5 µm 4.6×150 mm with precolumn at a column temperature of 40°. The elution solvents consisted of with acetonitrile (solvent A) and 10 mM octanesulfonic acid pH 3.0 (with phosphoric acid) containing 10% acetonitrile (solvent B). A gradient of 30% A to 100% A over 30 minutes, followed by 3 minutes at 100% A, was used. Injection volume was 10 µl and flow rate was 1 ml/min. Detection was performed with a Waters 2475 fluorescence detector using 340 nm for excitation and 510 nm for emission.

Figure 6:
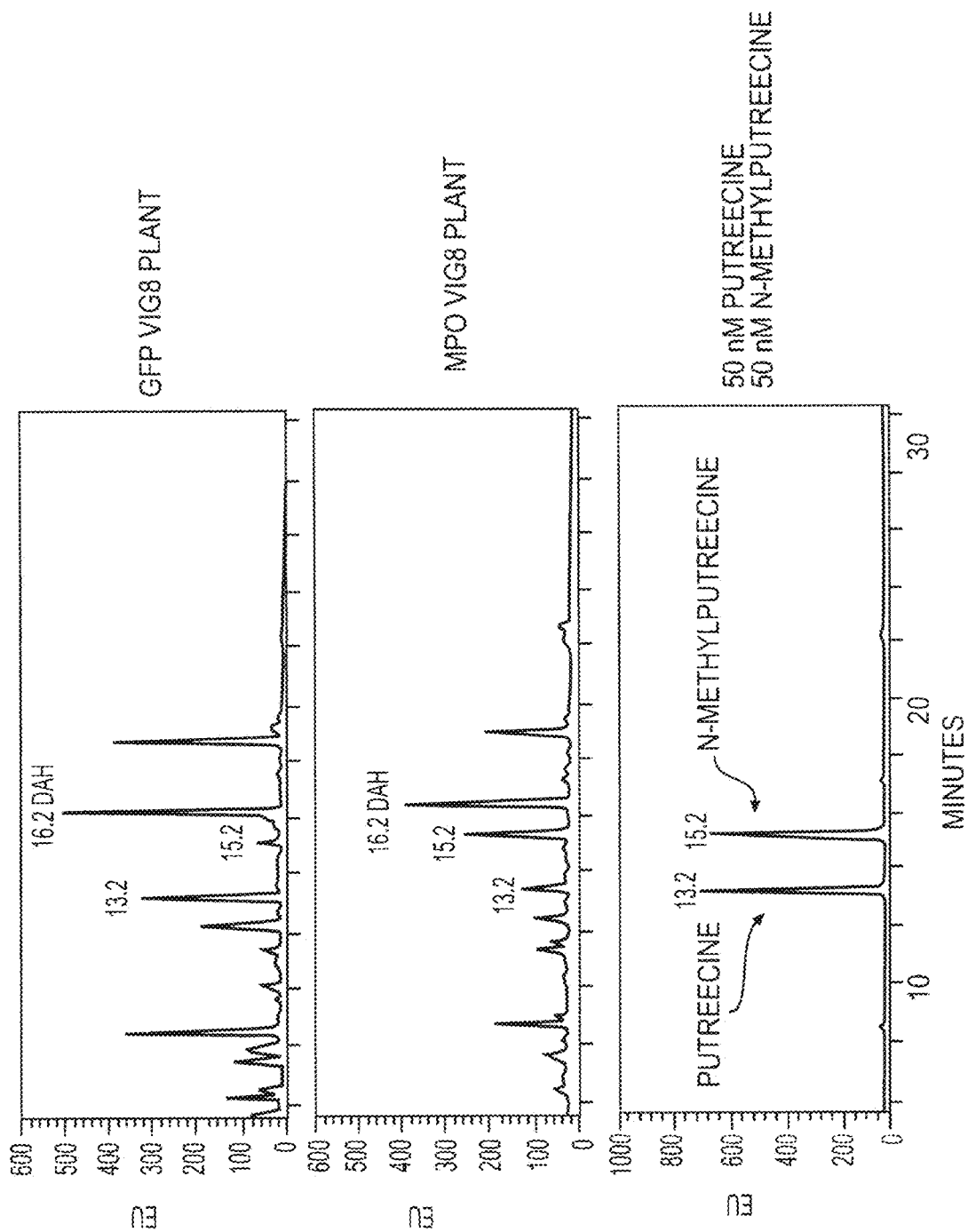
FIG. 6 depicts an HPLC analysis of N-methylputrescine in root tissue of plants treated with an MPO VIGS vector or with a control vector containing GFP sequences.

N-methylputrescine accumulates in the roots of *N. benthamiana* plants infected with the TRV-MPO silencing construct 214D11 (FIG. 6). The accumulation of the substrate for MPO in such plants further supports our assertion that our VIGS approach has identified the gene for an MPO enzyme that functions in nicotine biosynthesis. N-methylputrescine is also detectable at lower concentrations in TRV-GFP control plants.

Figure 7:
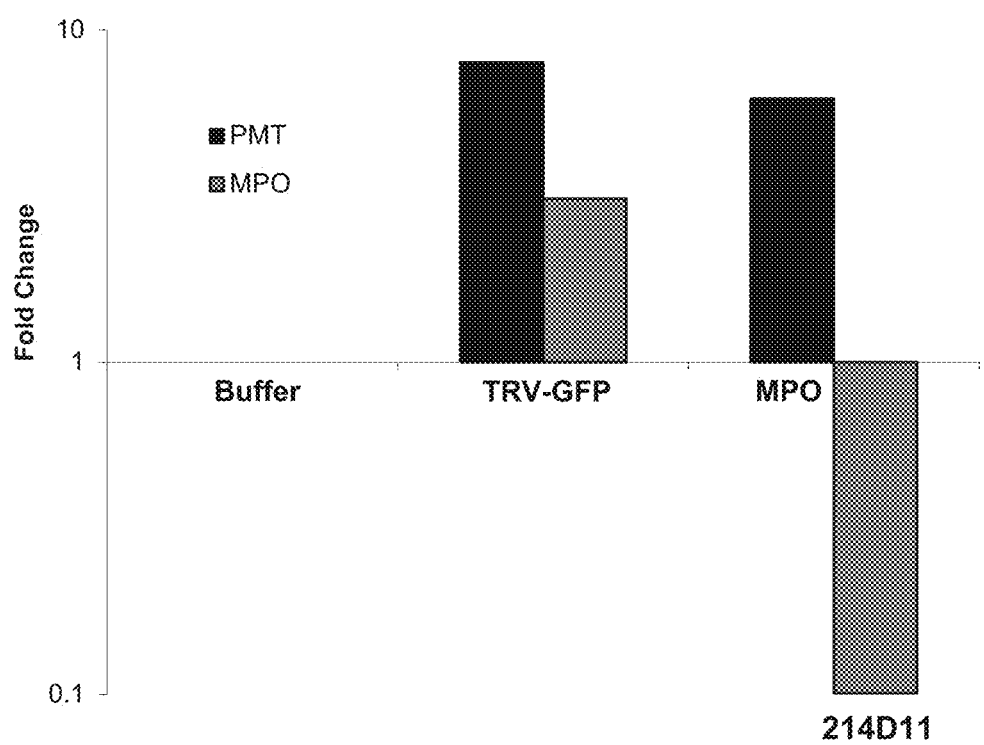
FIG. 7 depicts MPO transcript level in roots of plants treated with an MPO VIGS vector.

Measurement of MPO Expression in Plants Infected with MPO-VIGS Constructs qRT-PCR was used to measure the expression of MPO in the roots of plants that had been infected with TRV-MPO construct 214D11 or TRV-PMT construct. Roots were also sampled from buffer and TRV-GFP control plants. RNA isolation, cDNA synthesis and qRT-PCR conditions, including primer sequences, are described above. MPO and PMT expression increases in TRV-GFP plants compared to buffer control plants (FIG. 7) while the levels of MPO transcript are strongly reduced by silencing with TRV-MPO.

Assay of MPO Activity in Plants Infected with MPO-VIGS Constructs

Protein extracts was prepared from the roots of buffer control, TRV-GFP and TRV-MPO (214D11) infected plants. The extraction method described in Hashimoto T. et al. (Plant Physiol. 93: 216-221 (1990)) was used. Briefly, 1 g roots was ground in liquid nitrogen and suspended in 20 ml of extraction buffer containing 100 mM potassium phosphate pH 7.5, 0.25 M sucrose, 5 mM EDTA, 0.3% ascorbate and 10% PVPP. After centrifugation at 500 g for 30 min, the supernatant was further centrifuged at 11,000 g for another 30 minutes. The supernatant was subjected to two rounds of 20% and 40% ammonium sulphate precipitation. The precipitate was resuspended in 1 ml water, followed by dialysis overnight in 2 l of buffer containing 20 mM potassium phosphate pH 7.5, 1 mM DTT and 20% glycerol. The protein concentration was determined by DC protein assay kit (BioRad). An Amplex red hydrogen peroxide/peroxidase assay kit (Molecular Probes) was used to detect $H_2O_2$ generated by MPO after oxidation of N-methylputrescine. Briefly, a 50 µl reaction containing 8 µg of crude protein extract, 1 mM N-methylputrescine and 20 mM potassium phosphate buffer pH 7.5 was mixed with 50 µl $H_2O_2$ detection solution containing 0.1 mM Amplex red and 0.2 U/ml peroxidase. After incubating the mixture at 30° C. for 30 min, the fluorescence was measured with a fluorescence microplate reader (Victor3 UV multilabel reader, PerkinElmer) using excitation at 530-560 nm and emission at 590 nm.

Figure 8:
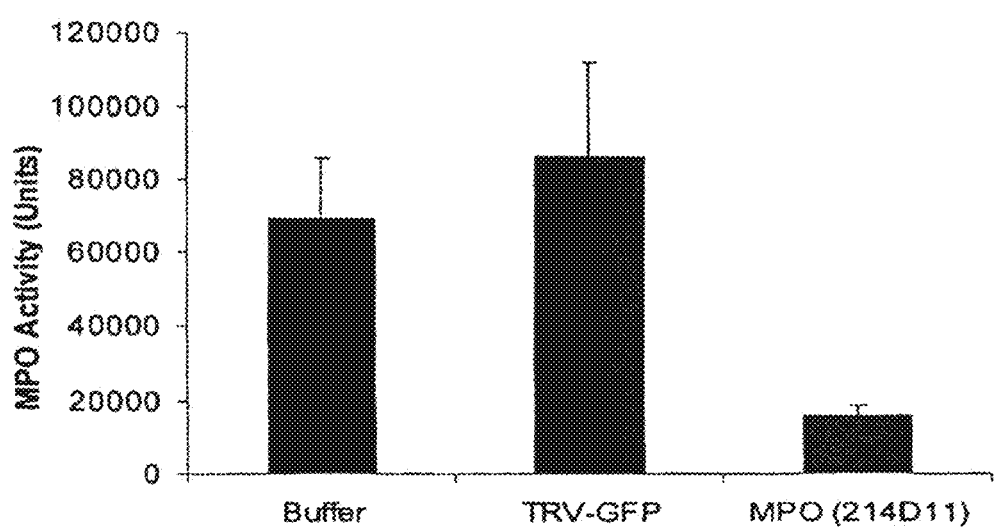
FIG. 8 depicts MPO activity in roots of plants treated with an MPO VIGS vector.

As shown in FIG. 8, MPO activity in the roots of TRV-MPO infected plants was lower than the activity found in buffer control and TRV-GFP plants.

Example 5. Characterization of the Catalytic Activity of Recombinant MPO

To conclusively show that the cloned gene encoded an MPO enzyme, its biochemical properties were characterized and the structure of the products formed during incubation of MPO with N-methylputrescine were determined.
Expression and Purification of Recombinant MPO The ORF of the *N. benthamiana* MPO was expressed in *E. coli* and the recombinant enzyme was purified for biochemical characterization. Primers 5'-ATGGCCAC-TACTAAACAGAAAG-3' and 5'-TAGTT-TAGCGGCCGCTCAAAGCTTGGCCAGCAAGCT-3' were designed to amplify the MPO ORF. Using first-strand cDNA as template, the cDNA clone was amplified using Pfu (Stratagene) and PCR conditions of 95° C. 30 sec, 58° C. 30 sec 72° C. 2.5 min for 35 cycles; the product was incubated with Taq polymerase 72° C. for 15 min to add A overhangs. The resulting PCR product was cloned into pCR8/GW/ TOPO vector (Invitrogen) to generate a Gateway entry clone, which was recombined with destination vector pHIS8GW by Gateway LR clonase (Invitrogen) to generate the expression clone pHIS8GW-MPO. The *E. coli* strain Rosetta (DE3) pLysS (Novagen) was transformed with pHIS8GW-MPO, which contains an N-terminal octahistidine fusion tag. A single colony was inoculated into 100 ml of overnight expression autoinduction system (Novagen) containing 50 µg/ml kanamycin and 34 µg/ml of chloramphenicol, and incubated at 28° C. with shaking overnight. Talon Superflow metal affinity resin (Clontech) was used for purification of recombinant MPO. After centrifugation of the overnight culture, the pellet was resuspended in 10 ml of lysis buffer containing 50 mM sodium phosphate buffer pH 8.0, 150 mM NaCl, 0.1% Triton-X100, 5 mM imidazole and protease inhibitor cocktail (Novagen). The cell suspension was sonicated for 2 minutes to lyse the bacteria. After centrifugation of the lysate at 12,000 rpm for 15 minutes, the supernatant was applied onto 200 µl Talon resin column. The column was washed with 30 ml of wash buffer containing 50 mM sodium phosphate pH 7.0, 150 mM NaCl and 10 mM imidazole, followed by elution with 10 ml of elution buffer containing 50 mM sodium phosphate pH 7.0, 150 mM NaCl and 200 mM imidazole. The fractions containing MPO were pooled and dialyzed against 2 L of storage buffer containing 50 mM potassium phosphate pH 7.5 and 50% glycerol. The protein concentration was determined with DC protein assay kit (BioRad) and MPO purity was analyzed with SDS-PAGE electrophoresis (BioRad). One mg of soluble MPO was obtained from 100 ml overnight culture.
Enzyme Assay of Recombinant MPO: Substrate Preferences Recombinant MPO was assayed using the Amplex red system described above, except that 1 µg of Talon purified MPO was used. To measure the kinetic parameters of MPO an assay with two fold serial dilutions of N-methylputrescine from 10 mM to 0.01 mM at 30° for 30 minutes was performed.

Substrate specificity experiments were carried out as above with 1 mM of N-methylputrescine, putrescine, diaminopropane, cadaverine, spermine and spermidine.

Figure 9:
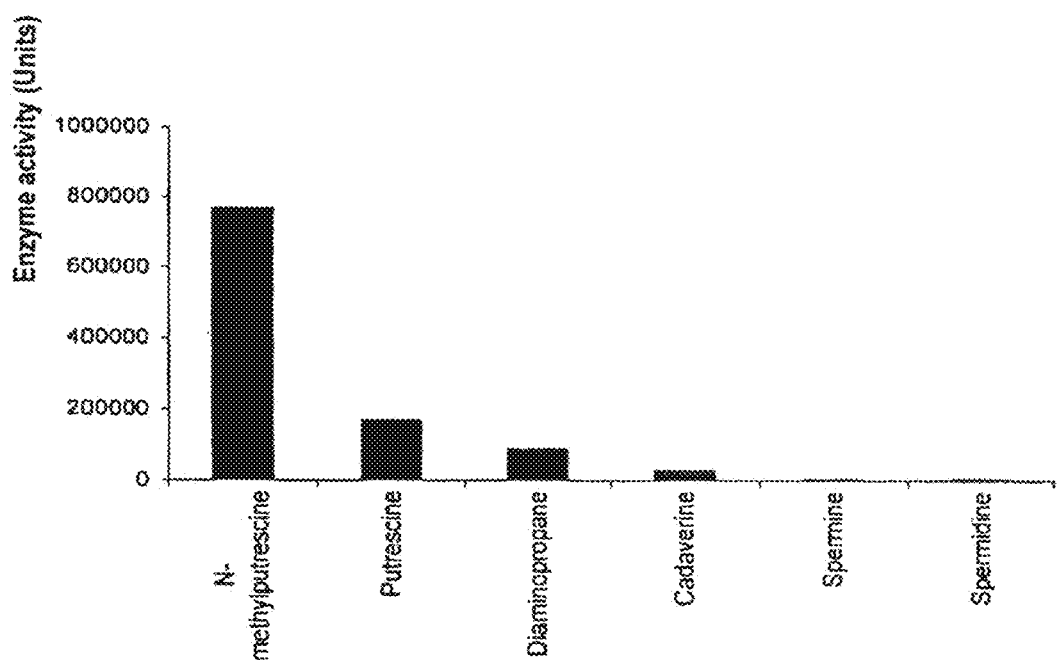
FIG. 9 depicts substrate specificity and enzyme kinetics of recombinant MPO.

The Km value for N-methylputrescine was determined to be 100 µM. Recombinant MPO preferred N-methylputrescine as a substrate (FIG. 9). The pH optimum of MPO, measured using 0.5 mM N-methylputrescine in 20 mM potassium phosphate buffer over the pH range 6.5, 7.0, 7.5, 8.0, 8.5 and 9.5, was 7.5.
Positive-Ion Electrospray Ionization Mass Spectrometric Analysis (ESI-MS) of MPO Reaction Product Mass spectrometry (MS) and gas chromatography-mass spectrometry (GC-MS) were used to determine the catalytic product formed by oxidation of N-methylputrescine by recombinant MPO.

For mass spectrometric analysis, a 50 µl reaction containing 1 µg purified MPO, 2 mM N-methylputrescine and 20 mM potassium phosphate buffer pH 7.5 was incubated at 30° C. for one hour, followed by MS analysis of product composition. A control reaction was performed using protein storage buffer instead of MPO solution. MS analysis was accomplished with positive-ion electrospray ionization mass spectrometry (ESI-MS) using a tandem quadrupole mass spectrometer (Quattro LC, Micromass, UK) fitted with a pneumatically-assisted electrospray ion source (Z-spray, Micromass). Samples were introduced by flow injection using a binary solvent pump and autosampler (1100 series, Hewlett Packard) operating at a flow rate of 20 µL/min. The carrier solvent consisted of 50:50 v/v methanol/water containing 0.1% formic acid.

Figure 10:
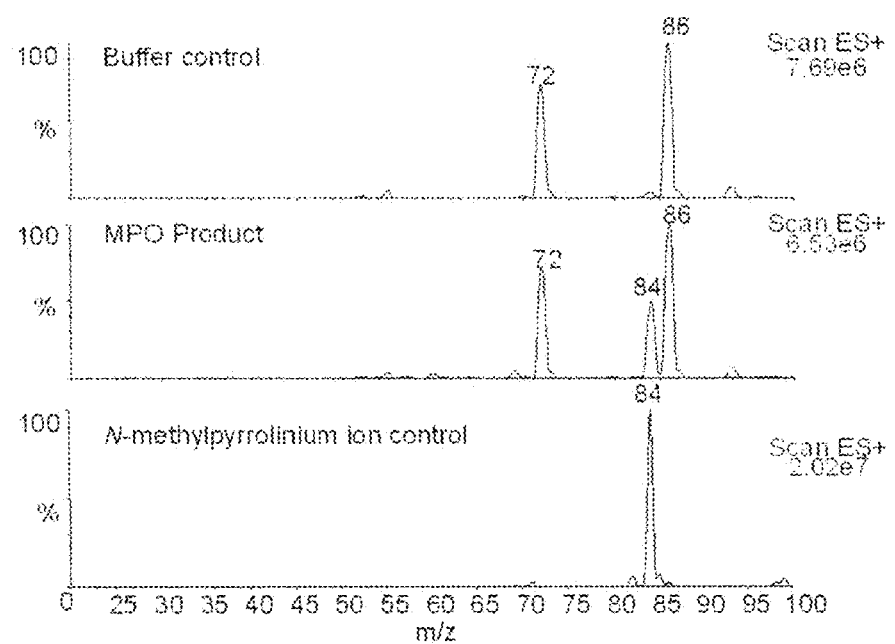
FIG. 10 depicts mass spectrometry analysis of the MPO product.
Figure 11:
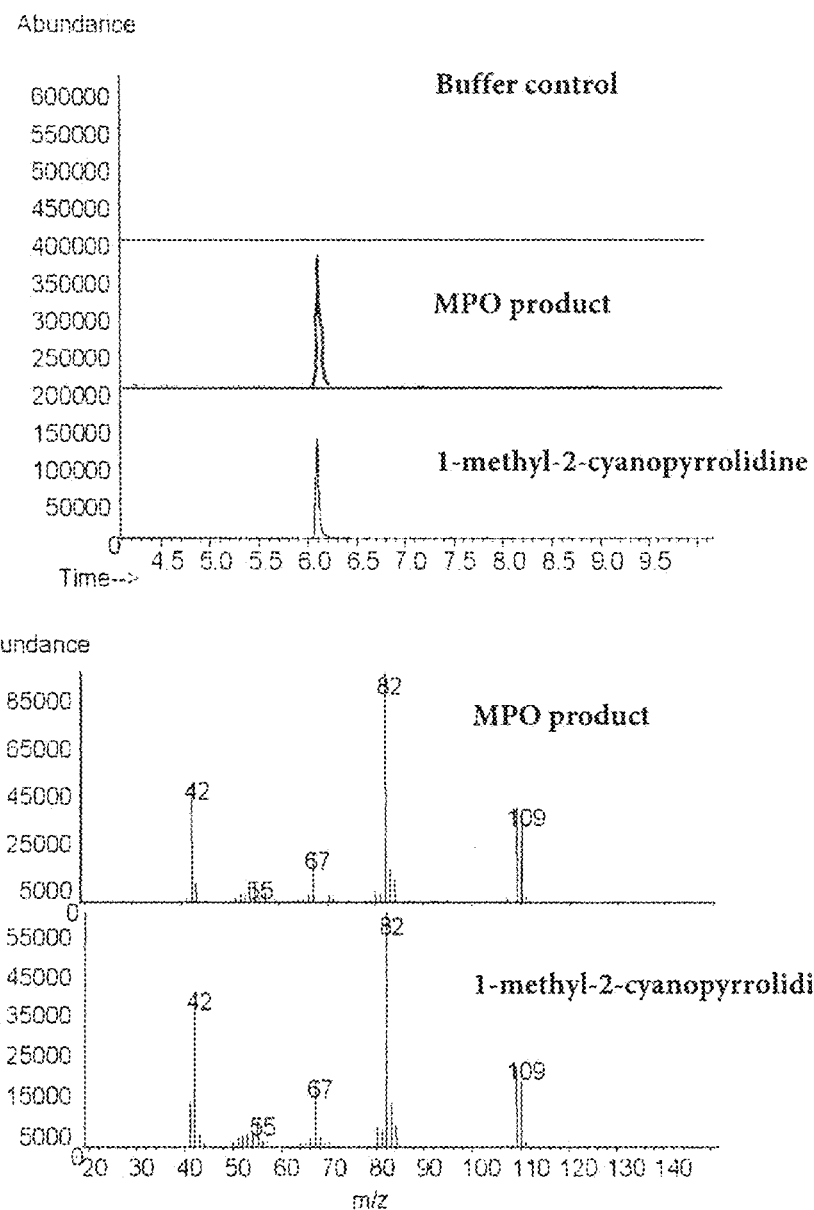
FIG. 11 depicts GC-MS analysis of derivatized MPO product.

The reaction product gave a peak of m/z 84 Da, which corresponds to the expected mass of N-methylpyrrolinium ion (FIG. 10).
GC-MS Analysis (ESI-MS) of MPO Reaction Product Cyanide trapping of N-methylpyrrolinium cation and GC-MS analysis was carried out as described in Hashimoto et al., (*Plant Physiol.* 93: 216-221 (1990)). Reaction of N-methylpyrrolinium ion with KCN yields 1-methyl-2-cyanopyrrolidine, which can be separated and analyzed by GC-MS. Briefly, the MPO reaction mixture was mixed with 10 µl of 10% KCN solution and incubated at room temperature for 30 minute, followed by addition of 100 µl of chloroform. After vortexing, the chloroform phase was analyzed by GC-MS. Authentic N-methylpyrrolinium cation was treated with KCN to yield a 1-methyl-2-cyanopyrrolidine reference compound. GC-MS analysis was accomplished using an Agilent 5973 mass selective detector coupled to an Agilent 6890N gas chromatograph equipped with a 30-m×0.25-mm DB5MS column with 0.25 µm film thickness (J&W Scientific). The system was controlled by G1701DA MSD ChemStation software. The chromatography conditions included a split injection (20:1) onto the column using a helium flow of 0.4 ml/min, an initial temperature of 70° C. for 1 minute, and a subsequent temperature ramp of 10° C./minute to 300° C. The mass selective detector was run under standard electron impact conditions (70 eV), scanning an effective m/z range of 40 to 700 at 2.26 scan/s.

GC-MS analysis of the 1-methyl-2-cyanopyrrolidine reference compound produced by cyanide trapping of N-methylpyrrolinium ion gave a peak at 6.1 min with a molecular ion of m/z 109. A peak of identical retention time (6.1 min) and mass spectrum was also present in the MPO reaction mixture. The mass spectra of each peak also had identical diagnostic ions that corresponded to those reported for 1-methyl-2-cyanopyrrolidine by Hashimoto et al., *Plant Physiol.* 93: 216-221 (1990). The detection of this product confirms that recombinant MPO catalyzes the oxidation of N-methylputrescine to form N-methylpyrrolinium ion.

Example 6. Stable Transformation of Plant with an MPO Overexpression Construct

*Nicotiana benthamiana* was transformed with an MPO overexpression construct. Primers 5'-ATGGCCAC-TACTAAACAGAAAG-3' and 5'-TAGTT-TAGCGGCCGCTCAAAGCTTGGCCAGCAAGCT-3' were designed to amplify the MPO ORF. Using first-strand cDNA as template, the cDNA clone was amplified using Pfu (Stratagene) and PCR conditions of 95° C. 30 sec, 58° C. 30 sec 72° C. 2.5 min for 35 cycles; the product was incubated with Taq polymerase 72° C. for 15 min to add A overhangs. The resulting PCR product was cloned into pCR8/GW/TOPO vector (Invitrogen) to generate a Gateway entry clone which was recombined with destination vector pK7GWG2 by Gateway LR clonase (Invitrogen) to generate the expression clone pK7GWG2-MPO. The clone was electroporated into *Agrobacterium tumefaciens* (C58) and plants were transformed using the leaf disc method (Draper et al, 1988). Transgenic plants were regenerated on selective agar media containing kanamycin and the transgenic status was confirmed using PCR analysis with primers designed to amplify the MPO transgene and promoter fusion (5'-ACTCCTCCCGTAAAATTTGTGA-3' and 5'-GCGGCCGCACTAGTGATATC-3') (FIG. 12). T1 seeds were grown in soil and leaf nicotine levels measured using ion-pair HPLC as described above. Nicotine was measured in samples containing three leaf discs (~50 mg FW), rather than on a fresh weight basis (FIG. 13).

The transgenic plants containing the MPO overexpression construct are screened to identify plants containing higher amounts of the MPO transcript and enzyme, and hence MPO activity. The amount of MPO transcript in transformed plants is determined using Northern blotting, RT-PCR or Real-time qRT-PCR. The amount of MPO enzyme is measured using Western blotting with an antibody specifically targeting the MPO protein, or using a variety of methods for quantifying protein content including proteomic analysis. The amount of MPO enzymatic activity in the MPO overexpressing plants, as measured by biochemical assay with N-methylputrescine as a substrate, is also used as a way to determine if the plants containing the MPO transgene produce higher amounts of the MPO protein. Plants with greater amount of MPO transcript, protein, and enzymatic activity, in comparison to wild-type plants or control plants transformed with vetor-only constructs, are useful for increased alkaloid varieties.

What is claimed is:

1. A method of producing N-methylpyrrolinium, comprising incubating N-methylputrescine with a recombinant MPO enzyme.

2. The method of claim 1, wherein the recombinant MPO enzyme has the amino acid sequence set forth in SEQ ID NO: 3, or a variant thereof, and the MPO enzyme is fused to a polyhistidine tag.

3. The method of claim 1, wherein the recombinant MPO enzyme is produced by:
   (1) genetically engineering a cell with a nucleic acid construct comprising an isolated nucleic acid molecule selected from the group consisting of:
       (a) the nucleotide sequence set forth in SEQ ID NO: 1;
       (b) the nucleotide sequence set forth in SEQ ID NO: 2;
       (c) a nucleotide sequence that encodes a polypeptide having the amino acid sequence set forth in SEQ ID NO: 3;
       (d) a nucleotide sequence that is at least 95% identical to the full length nucleotide sequences of (a), (b), or (c) and encodes an N-methylputrescine oxidase (MPO) enzyme;
       (e) a nucleotide sequence that hybridizes under high stringent conditions to the full length nucleotide sequences of (a), (b), (c), or (d) and encodes an MPO enzyme; and
       (f) a nucleotide sequence that differs from the nucleic acid sequence of (a) or (b) due to the degeneracy of the genetic code and encodes an MPO enzyme; and
   (2) growing the engineered cell under conditions such that MPO is produced.

4. The method of claim 3, wherein the genetically engineered cell is selected from the group consisting of bacteria, yeast, filamentous fungi, algae, green plants, insect, and mammalian cells.

5. The method of claim 3, wherein the isolated nucleic acid molecule is the nucleotide sequence set forth in SEQ ID NO: 1.

6. The method of claim 3, wherein the isolated nucleic acid molecule is the nucleotide sequence set forth in SEQ ID NO: 2.

7. The method of claim 3, wherein the isolated nucleic acid molecule is the nucleotide sequence that encodes a polypeptide having the amino acid sequence set forth in SEQ ID NO: 3.

8. The method of claim 5, wherein the nucleotide sequence set forth in SEQ ID NO: 1 is operably linked to a heterologous promoter sequence in the nucleic acid construct.

9. The method of claim 6, wherein the nucleotide sequence set forth in SEQ ID NO: 2 is operably linked to a heterologous promoter sequence in the nucleic acid construct.

10. The method of claim 7, wherein the nucleotide sequence that encodes a polypeptide having the amino acid sequence set forth in SEQ ID NO: 3 is operably linked to a heterologous promoter sequence in the nucleic acid construct.

11. The method of claim 8, wherein the genetically engineered cell is a bacterial cell.

12. The method of claim 9, wherein the genetically engineered cell is a bacterial cell.

13. The method of claim 10, wherein the genetically engineered cell is a bacterial cell.

14. The method of claim 11, wherein the bacterial cell is *Escherichia coli*.

15. The method of claim 12, wherein the bacterial cell is *E. coli*.

16. The method of claim 13, wherein the bacterial cell is *E. coli*.

17. A method of producing 1-methyl-2-cyanopyrrolidine, comprising:
   (a) incubating N-methylputrescine with a recombinant MPO enzyme; and
   (b) incubating the reaction product of (a) with KCN.

18. The method of claim 17, wherein the recombinant MPO enzyme has the amino acid sequence set forth in SEQ ID NO: 3, or a variant thereof, wherein the MPO enzyme is fused to a polyhistidine tag.

* * * * *